(12) United States Patent
Lee et al.

(10) Patent No.: US 8,450,469 B2
(45) Date of Patent: May 28, 2013

(54) SYNTHESIS OF PEPTIDE NUCLEIC ACIDS CONJUGATED WITH AMINO ACIDS AND THEIR APPLICATION

(75) Inventors: Hyunil Lee, Daejeon (KR); Jung Hyun Min, Daejeon (KR)

(73) Assignee: Panagene Inc., Daejeon (KR)

(*) Notice: Subject to any disclaimer, the term of this patent is extended or adjusted under 35 U.S.C. 154(b) by 272 days.

(21) Appl. No.: 12/810,453

(22) PCT Filed: Jan. 8, 2009

(86) PCT No.: PCT/KR2009/000087
§ 371 (c)(1), (2), (4) Date: Jun. 24, 2010

(87) PCT Pub. No.: WO2009/093821
PCT Pub. Date: Jul. 30, 2009

(65) Prior Publication Data
US 2011/0014715 A1    Jan. 20, 2011

(30) Foreign Application Priority Data
Jan. 21, 2008  (KR) .................. 10-2008-0006078

(51) Int. Cl.
C07H 21/00   (2006.01)
C07H 21/02   (2006.01)
C07H 21/04   (2006.01)
C12Q 1/68    (2006.01)
G01N 15/06   (2006.01)
G01N 31/22   (2006.01)

(52) U.S. Cl.
USPC ......... 536/23.1; 536/24.3; 536/25.3; 435/6.1; 422/50; 422/68.1; 422/430

(58) Field of Classification Search
USPC ........... 536/23.1, 25.3, 24.3; 435/6.1; 422/50, 422/430, 68.1
See application file for complete search history.

(56) References Cited

U.S. PATENT DOCUMENTS 5,719,262 A   2/1998   Buchardt et al.
6,204,326 B1  3/2001   Cook et al.
(Continued)

FOREIGN PATENT DOCUMENTS

| KR | 100464261 B1 | 1/2005 |
| KR | 1020070040420 A | 4/2007 |
| WO | 9825892 A1 | 6/1998 |

OTHER PUBLICATIONS

Keiko Ninomiya et al. In Situ Chemical Aminoacylation with Amino Acid Thioesters Linked to a Peptide Nucleic Acid; J. Am. Chem. Soc. 2004, 126, 15984-15989.*

(Continued)

*Primary Examiner* — Jezia Riley
(74) *Attorney, Agent, or Firm* — The Webb Law Firm

(57) ABSTRACT

This invention relates to a peptide nucleic acid (PNA) oligomer which is conjugated with one or more linear-type amino acid containing a plurality of alkyleneglycols and to a synthesis method thereof. In addition, this invention related to a linear amino acid spacer in a device for detection for detecting a target gene using the PNA oligomers which is fixed on a surface of a functionalized solid support. The linear amino acid spacer contains a plurality of alkyleneglycols and maintains enough space between the solid support and PNA oligomer in the device in order to prevent the interference of the interaction between the PNA oligomer and a target gene. Furthermore, this invention relates to a PNA array, a PNA chip and a gene diagnosis kit whereof sensitivity and specificity are improved by being manufactured with the PNA conjugated with the amino acid spacer.

14 Claims, 8 Drawing Sheets

U.S. PATENT DOCUMENTS

| | | | |
|---|---|---|---|
| 7,022,851 | B2 | 4/2006 | Kim et al. |
| 7,205,104 | B2 | 4/2007 | Remacle et al. |
| 7,282,329 | B2 | 10/2007 | Manalis et al. |
| 2004/0072208 | A1 | 4/2004 | Warthoe et al. |
| 2005/0026930 | A1 | 2/2005 | Kim et al. |
| 2006/0160731 | A1 | 7/2006 | Buchardt et al. |

OTHER PUBLICATIONS

Weiler et al., "Hybridisation based DNA screening on peptide nucleic acid (PNA) oligomer arrays", Nucleic Acids Research, 1997, pp. 2792-2799, vol. 25, No. 14.

Vilaivan et al., "Synthesis and properties of novel pyrrolidinyl PNA carrying β-amino acid spacers", Tetrahedron Letters, 2001, pp. 5533-5536, vol. 42.

Nielsen et al., "Sequence-Selective Recognition of DNA by Strand Displacement with a Thymine-Substituted Polyamide", Science, Dec. 6, 1991, pp. 1497-1500, vol. 254.

Brandt et al., "Peptide nucleic acids on microarrays and other biosensors", TRENDS in Biotechnology, Dec. 2004, pp. 617-622, vol. 22, No. 12.

Rockenbauer et al., "SNP Genotyping Using Microsphere-Linked PNA and Flow Cytometric Detection", Cytometry Part A, 2005, pp. 80-86, vol. 64A.

Uslu et al., "Labeifree fully electronic nucleic acid detection system based on a field-effect transistor device", Biosensors and Bioelectronics, 2004, pp. 1723-1731, vol. 19.

Hahm et al., "Direct Ultrasensitive Electrical Detection of DNA and DNA Sequence Variations Using Nanowire Nanosensors", Nano Letters, 2004, pp. 51-54, vol. 4, No. 1.

Macanovic et al., "Impedance-based detection of DNA sequences using a silicon transducer with PNA as the probe layer" Nucleic Acids Research, 2004, pp. 1-7, vol. 32, No. 2.

Schena, "Microarray Surfaces", Microarray Analysis, 2003, pp. 95-120.

Gabig et al., "An introduction to DNA chips: principles, technology, applications and analysis", Acta Biochimica Polonica, 2001, pp. 615-622, vol. 48, No. 3.

Pils et al., "Flexible non-nucleotide linkers as loop replacements in short double helical RNAs", Nucleic Acids Research, 2000, pp. 1859-1863, vol. 28, No. 9.

Shchepinov et al., "Steric factors influencing hybridisation of nucleic acids to oligonucleotide arrays", Nucleic Acids Research, 1997, pp. 1155-1161, vol. 25, No. 6.

Nielsen et al., "An Introduction to PNA", Peptide Nucleic Acids: Protocols and Applications, 2004, pp. 1-36.

Millican et al., "Synthesis and biophysical studies of short oligodeoxynucleotides with novel modifications: a possible approach to the problem of mixed base oligodeoxynucleotide synthesis", Nucleic Acids Research, 1984, pp. 7435-7453, vol. 12, No. 19.

Eritja et al., "Synthesis and properties of oligonucleotides containing 2'-deoxynebularine and 2'-deoxyxanthosine", Nucleic Acids Research, 1986, pp. 8135-8153, vol. 14, No. 20.

Seela et al., "Phosphoramidites of base-modified 2'-deoxyinosine isosteres and solid-phase synthesis of d(GCI*CGC) oligomers containing an ambiguous base", Nucleic Acids Research, 1986, pp. 1825-1844, vol. 14, No. 4.

Habener et al., "5-Fluorodeoxyuridine as an alternative to the synthesis of mixed hybridization probes for the detection of specific gene sequences", Proc. Natl. Acad. Sci., Mar. 1988, pp. 1735-1739, vol. 85.

Lin et al., "Synthesis and duplex stability of oligonucleotides containing cytosine-thymine analogues", Nucleic Acids Research, 1989, pp. 10373-10383, vol. 17, No. 24.

Loakes, "Survey and Summary the applications of universal DNA base analogues", Nucleic Acids Research, 2001, pp. 2437-2447, vol. 29, No. 12.

Dueholm et al., "Synthesis of Peptide Nucleic Acid Monomers Containing the Four Natural Nucleobases: Thymine, Cytosine, Adenine, and Guanine and Their Oligomerization", J. Org. Chem., 1994, pp. 5767-5773, vol. 59, No. 19.

Christensen et al., "Solid-phase Synthesis of Peptide Nucleic Acids", Journal of Peptide Science, 1995, pp. 175-183, vol. 3.

Thomson et al., "Fmoc Mediated Synthesis of Peptide Nucleic Acids", Tetrahedron, 1995, pp. 6179-6194, vol. 51, No. 22.

* cited by examiner

HBV1-F                    200bp
5' <u>ccatcatcttgggctttcgca</u>agattcctatgggagtgggcctcagtccgtttctcctggctcagtttactagtgc
catttgttcagtggttcgtagggcttttcccccactgtttgg|ctttcagttatatgga|tgatgtggtattgagggccaa
gtctgtacaacatcttgaatcccttttacca<u>ctgttaccaattttctttg</u> 3'
                                    HBV1-R HBV2-F                    530bp
5' <u>atgctgcaaggcgattaagt</u>tgggtaacgccagggttttcccagtcacgacgttgtaaaacgacggccagtg
aattgtaatacgactcactatagggcgaattgggcccgacgtcgcatgctcccggccgccatggccgcgggat
ccatcatcttgggctttcgcaagattcctatgggagtgggcctcagtccgtttctcctggctcagtttactag
tgccatttgttcagtggttcgtagggcttttcccccactgtttggcttt|cagttatatggatga|tgtggtattga
gggccaagtctgtacaacatcttgaatccctttttaccactgttaccaattttcttttgatcactagtgcggccg
cctgcaggtcgaccatatgggagagctcccaacgcgttggatgcatagcttgagtattctatagtgtcacctaaa
tagcttggcgtaatcatggtcatagctgtttcctgtgtgaaattgttatccgctcacaattccacacaaagcat<u>aaa
gtgtaaagcctggggtgcctaat</u> 3'
                HBV2-R HBV3-F                    773bp
5' <u>ttccaggcgccattcagg</u>ctgcgcaactgttgggaagggcgatcggtgcgggcctcttcgctattacgccagc
tggcgaaagggatgtgctgcaaggcgattaagttgggtaacgccagggttttcccagtcacgacgttgtaaaa
cgacggccagtgaattgtaatacgactcactatagggcgaattgggcccgacgtcgcatgctcccggccgcca
tggccgcgggatccatcatcttgggctttcgcaagattcctatgggagtgggcctcag|tccgtttctcctgg
ctcagtttactagtgccatttgttcagtggttcgtagggcttttcccccactgtttggcttt|cagttatatggat
ga|tgtggtattgagggccaagtctgtacaacatcttgaatccctttttaccactgttaccaattttcttttgatc
actagtgcggccgcctgcaggtcgaccatatgggagagctcccaacgcgttggatgcatagcttgagtattcta
tagtgtcacctaaatagcttggcgtaatcatggtcatagctgtttcctgtgtgaaattgttatccgctcacaattcca
cacaaagcataaagtgtaaagcctggggtgcctaatgagtgagctaactcacattaattgcgttgcgctcactgc
ccgcttttccagtcgggaaacctgtcgtgccagctgcattaatgaatcggccaacgcgcggggagaggcggttt
gcgtattgggcgctcttcc<u>gcttcctcgctcactgactc</u> 3'
                           HBV3-R HBV4-F                    1014bp
5' <u>agggaagaaagcgaaaggag</u>cgggcgctagggcgctggcaagtgtagcggtcacgctgcgcgtaacca
ccacacccgccgcgcttaatgcgccgctacagggcgcgtccaggcgccattcaggctgcgcaactgttgggaa
gggcgatcggtgcgggcctcttcgctattacgccagctggcgaaagggatgtgctgcaaggcgattaagttg
ggtaacgccagggttttcccagtcacgacgttgtaaaacgacggccagtgaattgtaatacgactcactatagg
gcgaattgggcccgacgtcgcatgctcccggccgccatggccgcgggatccatcatcttgggctttcgcaagat
tcctatgggagtgggcctcagtccgtttctcctggctcagtttactagtgccatttgttcagtggttcgtagggcttt
tcccccactgtttgg|ctttcagttatatgga|tgatgtggtattgagggccaagtctgtacaacatcttgaatcccttttt
accactgttaccaattttcttttgatcactagtgcggccgcctgcaggtcgaccatatgggagagctcccaacgcg
ttggatgcatagcttgagtattctatagtgtcacctaaatagcttggcgtaatcatggtcatagctgtttcctgtgtg
aaattgttatccgctcacaattccacacaaagcataaagtgtaaagcctggggtgcctaatgagtgagctaactc
acattaattgcgttgcgctcactgcccgcttttccagtcgggaaacctgtcgtgccagctgcattaatgaatcggcc
aacgcgcggggagaggcggtttgcgtattgggcgctcttccgcttcctcgctcactgactcgctgcgctcggtc
gttcggctgcggcgagcggtatcagctcactcaaaggcggtaatacggttatccacagaatcaggggataacg
caggaaa<u>gaacatgtgagcaaaaggcc</u> 3'
                HBV4-R

Figure 6

P/M ratio = perfect match signal /mismatch signal

SYNTHESIS OF PEPTIDE NUCLEIC ACIDS CONJUGATED WITH AMINO ACIDS AND THEIR APPLICATION

TECHNICAL FIELD

The following disclosure relates to a peptide nucleic acid (hereinafter, 'PNA') oligomer conjugated with one or more long linear chain amino acid(s) having a plurality of alkylene glycols as a spacer and a method for synthesizing the same.

The disclosure also relates to a long linear chain amino acid spacer having a plurality of alkylene glycols allowing to maintain a sufficient distance between a solid support and a PNA oligomer when manufacturing a PNA array using the PNA oligomer, thereby ensuring a space for effective interaction with a target gene.

The disclosure further relates to a PNA array, a PNA chip and a kit for genetic diagnosis with improved sensitivity and specificity, manufactured using the PNA conjugated with the amino acid spacer.

BACKGROUND ART

Peptide nucleic acid (PNA) is a DNA analogue linked by peptide bonds, not by phosphate bonds, and was first reported in 1991 [Nielsen P E, Egholm M, Berg R H, Buchardt O, "Sequence-selective recognition of DNA by strand displacement with a thymine-substituted polyamide", *Science* 1991, Vol. 254: pp. 1497-1500] (FIG. 1). PNA is synthesized chemically and is not known to occur naturally. PNA hybridizes to a naturally occurring nucleic acid with a complementary base sequence to form a double strand. Given the same number of nucleic acid bases, a PNA/DNA double strand is more stable than a DNA/DNA double strand, and a PNA/RNA double strand is more stable than a DNA/RNA double strand. The most frequently used backbone of PNA is repeating N-(2-aminoethyl)glycine units linked by amide bonds. The PNA's backbone is electrically neutral, whereas naturally occurring nucleic acids are negatively charged. The four nucleobases of PNA occupy similar spaces to those of DNA, and the distance between the nucleobases is almost identical to that in the naturally occurring nucleic acids. PNA is not only chemically more stable than naturally occurring nucleic acids but also biologically more stable since it is not degraded by nucleases or proteases. Also, because PNA is electrically neutral, the stability of the PNA/DNA and PNA/RNA double strands is not affected by salt concentration. For these reasons, PNA better recognizes complementary base sequences than naturally occurring nucleic acids and is utilized for diagnosis or other biological or medical applications.

In general, when a sequence of nucleobase is recognized or detected in a homogeneous solution using a probe with a known base sequence, only one sequence can be recognized at a time, and it is difficult to detect several sequences at once using fluorescent dyes of different colors. In contrast, by immobilizing a great number of probes on a solid surface, a number of specific sequences of nucleobase may be detected at once. A DNA microarray on which hundreds of thousands of probes are two-dimensionally arranged is commercially available. Also, a PNA microarray or a PNA chip using a PNA probe instead of a DNA probe is known [Brandt O, Hoheisel J D, "Peptide nucleic acids on microarrays and other biosensors" *Trends Biotechnology* 2004, Vol. 22, pp. 617-622]. A technique of immobilizing PNA probes on the surface of microbeads (or microspheres) of several μm size to carry out detection is also known [Rockenbauer E, Petersen K H, Vogel U, Bolund L, Kølvraa S, Nielsen K V, Nexø B A, "SNP genotyping using microsphere-linked PNA and flow cytometric detection" *Cytometry Part A* 2005, Vol. 64A, pp. 80-86]. Although a technique of identifying hybridization of a probe to a complementary sequence of nucleobase using fluorescence is widely used, a technique of detecting a sequence of nucleobase electrically using a field-effect transistor using PNA immobilized on a silicon semiconductor or silicon nanowire is also known [F. Uslu et al. "Labelfree fully electronic nucleic acid detection system based on a field-effect transistor device", *Biosensors and Bioelectronics* 2004, Vol. 19 pp. 1723-1731; J. Hahm and C. M. Lieber, "Direct ultrasensitive electrical detection of DNA and DNA sequence variations using nanowire nanosensors", *Nano Letters* 2004, Vol. 4, pp. 51-54]. Also, an apparatus for detecting a sequence of nucleobase based on impedance change is reported [A. Macanovic et al. "Impedance-based detection of DNA sequences using a silicon transducer with PNA as the probe layer", *Nucleic Acids Research* 2004, Vol. 32, p. 20].

Since the mass of a probe changes before and after hybridization to a target nucleic acid, a sequence of nucleobase may be detected based on the mechanical change resulting therefrom. Also, detection can be made based on the fact that the vibration frequency of a microcantilever or a surface acoustic wave (SAW) sensor changes before and after binding to DNA or RNA. A microcantilever and a SAW sensor using PNA are reported [S. Manalis and T. Burg, U.S. Pat. No. 7,282,329 "Suspended microchannel detectors"; P. Warthoe and S. Iben, US Patent Application Publication No. 2004/0072208 A1 "Surface acoustic wave sensors and method for detecting target analytes"].

Such apparatuses or methods of detecting base sequences using a plurality of PNA probes require immobilization of the PNA probes on solid surface. For the immobilization, stable chemical covalent bonding is more frequently employed than physical bonding. In general, immobilization using a covalent bonding such as aldehyde-amine bonding, carboxylic acid-amine bonding or epoxide-amine bonding is widely employed for immobilization of a biochip such as a PNA chip, a DNA chip, a protein chip, or the like [M. Schena, Microarray analysis, A John Wiley & Sons, Inc., Publication, pp. 95-120]. In order to immobilize PNA on glass surface, the glass surface is often subject to silylation by an organosilane substance having an aldehyde, amine or epoxy group so that the functional group is exposed on the glass surface. Then, the N-terminal amine group of PNA is reacted with the exposed functional group to form a covalent bonding.

When a probe is immobilized on the solid surface, if the probe is too close to the support, steric hindrance may occur during hybridization of the probe to the target gene. A spacer is interposed between the probe and the solid support to solve this problem. A nucleotide spacer linked by phosphate bonding and an amino acid spacer with a relatively short chain may be used for this purpose. The spacer greatly influences the interaction of the probe with the target substance depending on its length, charge, hydrophobicity, solvation property or the like.

In a DNA chip, a nucleotide spacer linked by phosphate bonding is mainly used to improve sensitivity and specificity of target gene detection [Magdalena Gabig, *Acta Bio. Polonica,* 2001, 48, 615]. However, the nucleotide spacer linked by phosphate bonding is problematic in that it is not applicable to a PNA having a backbone linked by amide bonding since it lacks amine, carboxylic acid or ester residues that form amide bonding. In addition, the phosphate anion decreases the efficiency of hybridization [W. Pils and R. Micura, *Nucleic Acids Research,* 2000, 28, 1859.; U.S. Pat. No. 7,205,104]. Further, a spacer having positive or negative charge is known to have decreased efficiency of hybridization as compared to a neutral spacer [M. S. Shchepinov, *Nucleic Acids Research*, 1997, 25, 1155]. For this reason, neutral amino acid derivatives with linear structure such as 8-amino-3,6-dioxaoctanoic acid that can form amide binding with PNA were introduced. By synthesizing a probe by polymerizing several 8-amino-3,6-dioxaoctanoic acids with a PNA oligomer and immobilizing it on a support, thereby ensuring a space between the support and the PNA oligomer, the efficiency of hybridization may be improved.

However, because 8-amino-3,6-dioxaoctanoic acid has a short length, polymerization of 8-amino-3,6-dioxaoctanoic acid to the PNA oligomer has to be repeated for 4-5 times or more to ensure a sufficient distance between the support and PNA. Thus, there is a need for using a longer spacer so that a sufficient distance between the PNA oligomer and the support can be ensured without having to perform the polymerization several times.

DISCLOSURE

Technical Problem

An embodiment of the present invention is directed to providing a peptide nucleic acid (PNA) conjugated with a long linear chain amino acid having a plurality of alkylene glycols, which is longer than the existing amino acid spacer, and a method for preparing the same.

An embodiment of the present invention is also directed to providing a long linear chain amino acid having a plurality of alkylene glycols.

An embodiment of the present invention is also directed to providing a method for immobilizing the PNA conjugated with the amino acid spacer on a functionalized surface to improve sensitivity and specificity, and a PNA chip and a kit for genetic diagnosis with improved sensitivity and specificity prepared by immobilizing on a surface of a functionalized plastic substrate or a solid substance such as silica, semiconductor, magnetic particles, nylon, polymer compound, thin film, cellulose or nitrocellulose, as well as a functionalized glass substrate, using the immobilization method.

Technical Solution

The present invention relates to a PNA oligomer conjugated with one or more long linear chain amino acid(s) having a plurality of alkylene glycols as a spacer, a method for synthesizing the same, and applications thereof. More specifically, a long linear chain amino acid derivative having a plurality of alkylene glycols is conjugated at the amine (N)-terminus of the functional molecule PNA to prepare a PNA probe. As a result, a sufficient distance is ensured between the surface of a support and the PNA oligomer, which results in improved sensitivity and specificity of detection of a target gene as well as solubility.

The present invention also relates to a long linear chain amino acid spacer having a plurality of alkylene glycols allowing to maintain a sufficient distance between a solid support and a PNA oligomer when manufacturing a PNA array using the PNA oligomer, thereby ensuring a space for effective interaction with a target gene. The amino acid spacer may further have a linear or branched chain.

The present invention further relates to a PNA array, a PNA chip and a kit for genetic diagnosis with improved sensitivity and specificity, which is prepared using the PNA conjugated with the amino acid spacer.

Hereinafter, exemplary embodiments will be described in detail.

The peptide nucleic acid (PNA) used in the present invention is an artificially synthesized DNA analogue, with the backbone of DNA replaced by the amide N-(2-aminoethyl) glycine repeat units and is represented by the following structural formula. It was first reported in 1991 by Buchardt, Nielsen, Egholm, Berg and others and has superior physical properties over DNA.

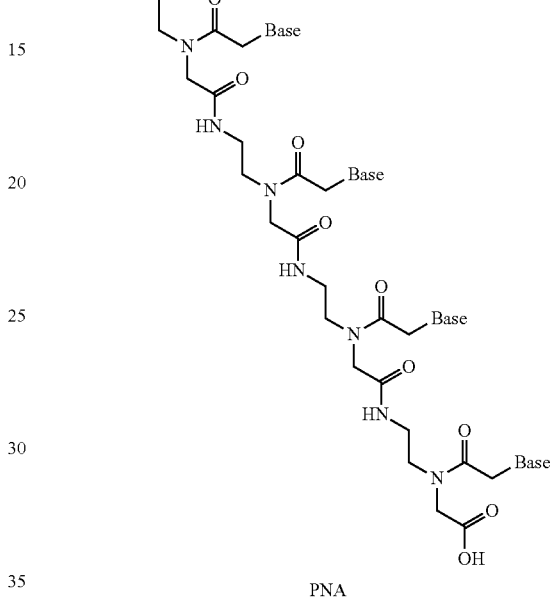

PNA

Although the PNA having repeating N-(2-aminoethyl)glycine units as a backbone is the most commonly used, PNAs of the following structures are also known [P. E. Nielsen and M. Egholm "An Introduction to PNA" in P. E. Nielsen (Ed.) "Peptide Nucleic Acids: Protocols and Applications" 2nd Ed. Page 9 (Horizon Bioscience, 2004)]. These PNAs may also be employed in the present invention.

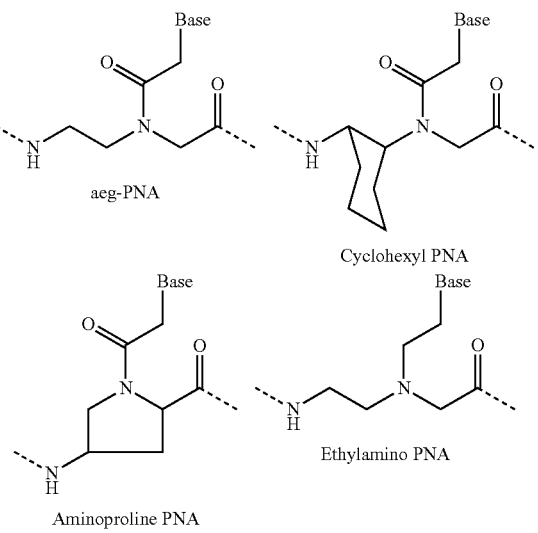

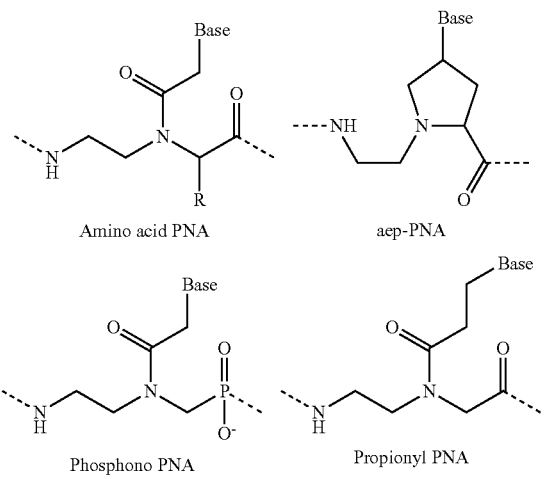

Amino acid PNA    aep-PNA

Phosphono PNA    Propionyl PNA

Preferably, the PNA oligomer used in the present invention is a PNA oligomer having 8 to 40 nucleobases, and may be represented by the following structural formula:

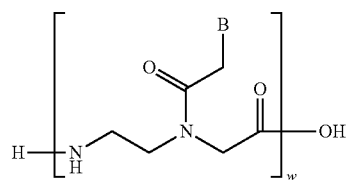

In the formula above, B is a naturally occurring or synthetic nucleobase. Specifically, the naturally occurring nucleobase may be thymine, cytosine, adenine or guanine, and w is an integer from 8 to 40. The synthetic nucleobase includes 2,6-diaminopurine, pseudoisocytosine, 2-thiouracil, 5-bromouracil, inosine, or the like. Further, universal bases that can bind to various nucleobases such as 1,2-dideoxy-D-ribofuranose and 1,2-dideoxy-1-phenyl-β-D-ribofuranose [T. A. Millican et al. *Nucleic Acids Research*, 1984, 12, 7435-7453], hypoxanthine, xanthine and deaminated guanine [R. Eritja et al., *Nucleic Acids Research*, 1986, 14, 8135-8153], 2'-deoxyinosine [F. Seela and K. Kaiser, *Nucleic Acids Research*, 1986, 14, 1825-1844], 5'-fluorodeoxyuridine [J. F. Habener et al., 1988, *Proceedings of the National Academy of Sciences*, 85, 1735-1739], methoxycytosine, 6H,8H-3,4-dihydro-pyrimido[4,5-c][1,2]oxazin-7-one [P. K. T. Lin and D. M. Brown., 1989, *Nucleic Acids Research*, 17, 10373-10383], or the like are included. Examples of more universal bases are described in D. Loakes, "Survey and Summary: The applications of universal DNA base analogues", *Nucleic Acids Research*, 2001, vol. 29 pp. 2437-2447.

A PNA conjugated with an amino acid spacer according to the present invention is represented by Chemical Formula 1.

[Chemical Formula 1]

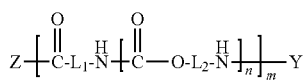

In Chemical Formula 1, Z is a PNA oligomer with 8 to 40 nucleobases, and the amine (N)-terminus of the PNA oligomer is bonded to a carbonyl group; $L_1$ and $L_2$ are independently a chemical bond or linear or branched $C_1$-$C_{15}$ alkylene, and the carbon atom of the alkylene may be further substituted with 1 to 8 oxygen (O) atom(s); Y is hydrogen or a linker for immobilization onto a support; and m and n are independently an integer from 1 to 10.

Wherein the alkylene is an alkanediyl functional group. Any of a series of divalent radicals of the general formula CnH2n derived from aliphatic hydrocarbons. Unless specified otherwise, such alkanediyls include substituted alkanediyls.

The linker Y for immobilization onto a support may be represented by the following structural formula:

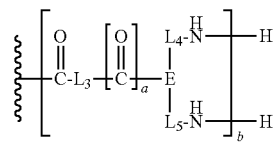

In the formula above, $L_3$, $L_4$ and $L_5$ are independently a chemical bond or $C_1$-$C_{10}$ alkylene, and the carbon atom of the alkylene may be further substituted with 1 to 3 oxygen atom(s); E is CH or N; a is 0 or 1; and b is an integer from 2 to 10.

Preferably, Y is a linker wherein $L_3$, $L_4$ and $L_5$ are independently a chemical bond —$CH_2$—, —$CH_2CH_2$—, —$CH_2CH_2CH_2$— or —$CH_2CH_2CH_2CH_2$—, E is CH or N, b is an integer from 2 to 7, and a is 0 or 1. It may be represented by the following structures, but is not limited thereto:

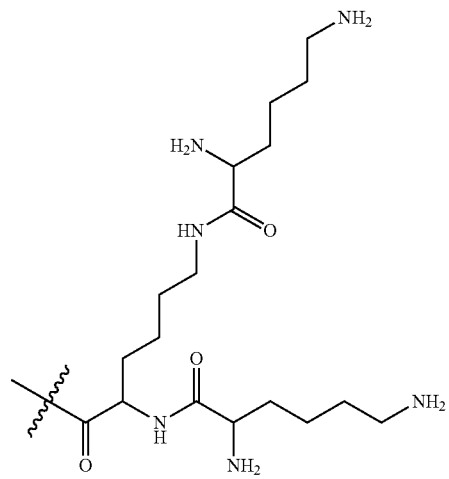

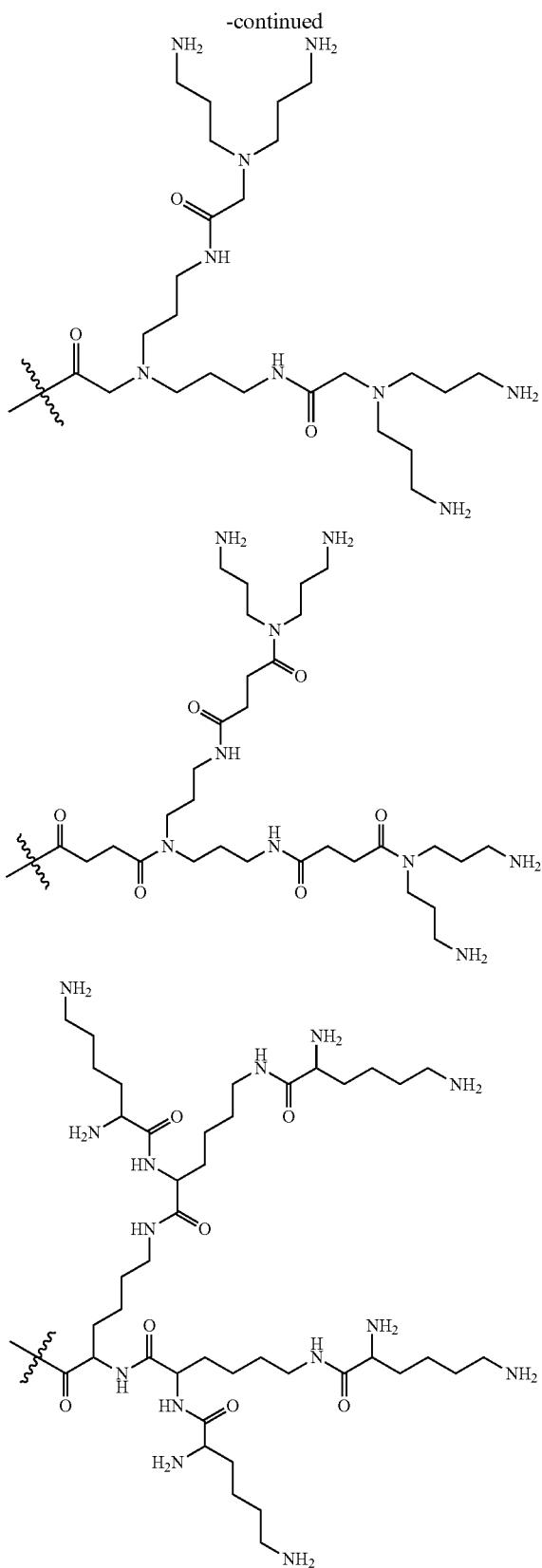

10 times to prepare a PNA conjugated with an amino acid spacer, which is represented by Chemical Formula 3.

[Chemical Formula 2]

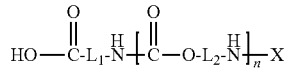

In Chemical Formula 2, $L_1$ and $L_2$ are independently a chemical bond or linear or branched $C_1$-$C_{15}$ alkylene, and the carbon atom of the alkylene may be further substituted with 1 to 8 oxygen atom(s); X is hydrogen or an amine protecting group; and n is an integer from 1 to 10.

[Chemical Formula 3]

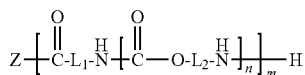

In Chemical Formula 3, Z is a PNA oligomer having 8 to 40 nucleobases, and the amine (N)-terminus of the PNA oligomer is bonded to carbonyl; $L_1$ and $L_2$ are independently a chemical bond or linear or branched $C_1$-$C_{15}$ alkylene, and the carbon atom of the alkylene may be further substituted with 1 to 8 oxygen atom(s); and m and n are independently an integer from 1 to 10.

Further, according to the present invention, a PNA conjugated with an amino acid spacer, which is represented by Chemical Formula 3, is sequentially reacted with an immobilization linker represented by Chemical Formula 4 for 2 to 10 times to prepare a PNA conjugated with an amino acid spacer with the immobilization linker attached, which is represented by Chemical Formula 5.

[Chemical Formula 4]

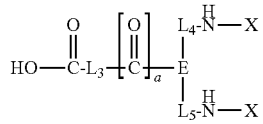

[Chemical Formula 5]

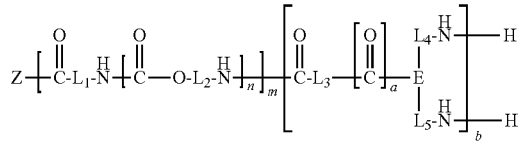

In Chemical Formulae 4 and 5, Z is a PNA oligomer having 8 to 40 nucleobases, and the amine (N)-terminus of the PNA oligomer is bonded to carbonyl; $L_1$ and $L_2$ are independently a chemical bond or linear or branched $C_1$-$C_{15}$ alkylene, and the carbon atom of the alkylene may be further substituted with 1 to 8 oxygen atom(s); $L_3$, $L_4$ and $L_5$ are independently a chemical bond or $C_1$-$C_{10}$ alkylene, and the carbon atom of the alkylene may be further substituted with 1 to 3 oxygen atom(s); E is CH or N; X is an amine protecting group; a is 0 or 1; b is an integer from 2 to 10; and m and n are independently an integer from 1 to 10.

A commonly used amine protecting group may be used to protect the amine group of the amino acid monomer resented by Chemical Formula 2 or the immobilization linker represented by Chemical Formula 4. Specifically, the amine protecting group may be t-butoxycarbonyl (Boc), 9H-fluoren-9-

According to the present invention, a PNA oligomer having 8 to 40 nucleobases is sequentially reacted with an amino acid spacer monomer represented by Chemical Formula 2 for 1 to ylmethoxycarbonyl (Fmoc), trityl, benzyl, chloroacetyl, benzyloxycarbonyl, p-methoxybenzyloxycarbonyl, formyl, trifluoroacetyl, p-toluenesulfonyl, benzenesulfonyl, methanesulfonyl, p-nitrobenzyloxycarbonyl, 2,2,2-trichloroethoxycarbonyl, or the like.

Preferably, the amino acid monomer resented by Chemical Formula 2 is one with $L_1$ being —$CH_2$—, $L_2$ being —$CHH_2CH_2OCH_2CH_2$—, and n being 2, 4 or 6. It may be represented by Chemical Formula 2-1, but is not limited thereto.

[Chemical Formula 2-1]

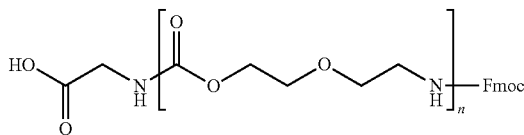

In Chemical Formula 2-1, n is 2, 4 or 6.

The amino acid monomer represented by Chemical Formula 2 may be prepared, for example, as follows. As seen in FIGS. 3 to 5, 2-(2-aminoethoxy)ethanol having an amine group and an alcohol at either end is used as a precursor. After protecting the amine group with a protecting group, the precursor is reacted with 4-nitrophenyl chloroformate to convert the terminal alcohol group into an activated carbonate. The activated carbonate is reacted with the amine group of 2-(2-aminoethoxy)ethanol to prepare a carbamate. This alcohol activation and reaction with aminoalcohol may be repeated to prepare linear amino acid spacer monomers of various lengths having various alkylene glycols in addition to ethylene glycol.

The PNA oligomer used in the present invention may be synthesized according to the method disclosed in Korean Patent Publication No. 2007-0040420 from a PNA monomer protected with a Bts (benzothiazolesulfonyl) group. Further, it may be synthesized from a PNA monomer protected with a 9-fluorenylmethyl carbamate (Fmoc) group or a t-butoxycarbonyl (Boc) group [*J. Org. Chem.*, 59, 5767-5773, *J. Peptide Sci.* 3, 175-183, *Tetrahedron Letters*, 22, 6179-6194]. The scope of the present invention is not limited by the PNA synthesis method.

FIG. 2 shows a solid-phase synthesis process of a PNA oligomer according to the present invention. The PNA oligomer is synthesized from a PNA monomer protected with a Bts group and a functionalized resin according to the method of Korean Patent No. 10-0464261. The synthesis procedure consists of the three steps of removing the protecting group bound to the amine group of the PNA, coupling (or conjugating) the PNA or the amino acid spacer monomer to the PNA, and deactivating the unreacted amine group by capping.

The PNA conjugated with an amino acid spacer according to the present invention may be immobilized on a functionalized solid surface to prepare a PNA chip array, a kit for genetic diagnosis, or the like. Preferably, the solid substance may be glass substrate, silica, semiconductor, magnetic particles, nylon, polymer compound such as poly(dimethylsiloxane) (PDMS), cellulose or nitrocellulose, but is not limited thereto. The surface of the solid substance may be functionalized with such functional group as an aldehyde group, a carboxylic acid group, an epoxy group, an isothiocyanate group, an N-hydroxysuccinimidyl (NHS) group or an activated ester group.

The PNA conjugated with an amino acid spacer oligomer according to the present invention may be bound on glass, silica, semiconductor, magnetic particles, plastic, gold or silver tube, thin film, porous filter or bead to be used as a chip. The PNA conjugated with an amino acid spacer according to the present invention may be immobilized on a functionalized solid substance to manufacture an apparatus for detecting or analyzing sequence of nucleobases. Such apparatus includes a PNA microarray in which a plurality of PNA probes are two-dimensionally arranged, a PNA chip, a microbead of several gm size on which the PNA is immobilized, a field-effect transistor in which the PNA is immobilized on silicon semiconductor or silicon nanowire, an impedance detector, a microcantilever, a surface acoustic wave (SAW) sensor, or the like, but is not limited thereto.

Reaction and analysis conditions for the PNA chip to investigate the effect of the amino acid spacer of the present invention are established as follows.

(a) A reaction sample including target DNA is added to the PNA chip.

(b) The PNA probe and the target DNA are subject to hybridization.

(c) A signal resulting from the PNA/DNA hybridization is detected.

In the step (a), target DNAs with various lengths are prepared using a primer with biotin attached at the end thereof.

In the step (b), it is preferred to use a hybridization buffer containing the ingredients facilitating the hybridization of the PNA probe and the target DNA. Preferably, the hybridization is carried out by adding streptavidin-Cy5 which binds to the biotin labeled at the end of the primer and produces color. Following the hybridization, it is preferred to effectively remove unreacted remaining target DNA and nonspecific reaction products using a washing buffer.

In the step (c), an optical, electrochemical or other detection means capable of detecting a signal resulting from the DNA/DNA hybridization may be used. For instance, cyanine 5 (Cy5), biotinylated compound, cyanine 3 (Cy3), or the like are included, but the present invention is not limited thereto. Preferably, streptavidin-Cy5 is used to scan the fluorescence emitted as it is bound to the biotin attached at the end of the target DNA.

DESCRIPTION OF DRAWINGS

FIG. 6 shows DNA base sequences of complementary PCR products prepared using different PNA probes.

MODE FOR INVENTION

Figure 1:
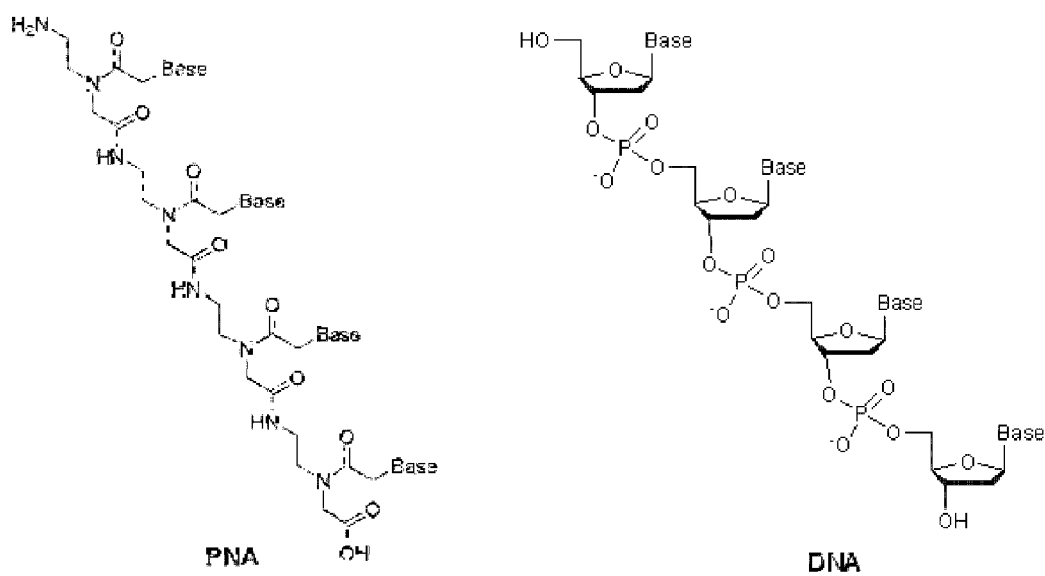
FIG. 1 shows structural formula of peptide nucleic acid (PNA) and DNA.
Figure 2:
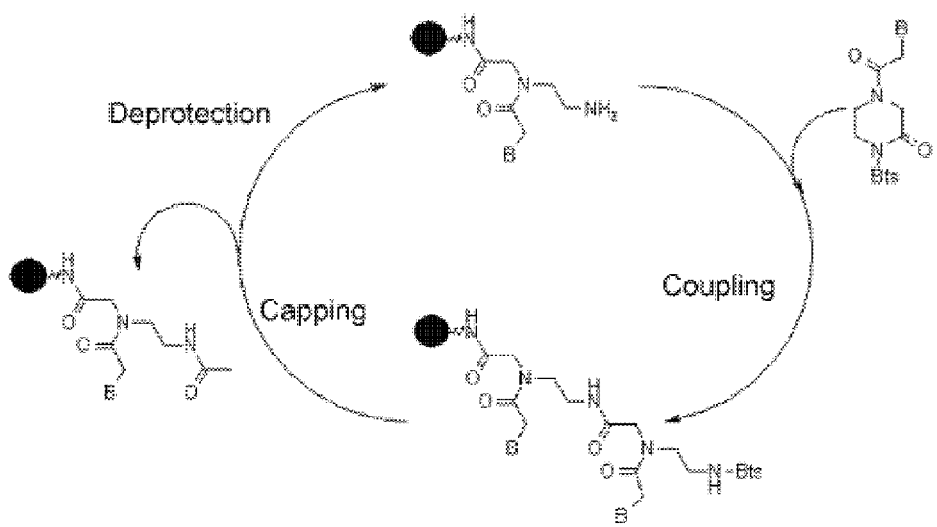
FIG. 2 shows a solid-phase synthesis process of a PNA oligomer.
Figure 3:
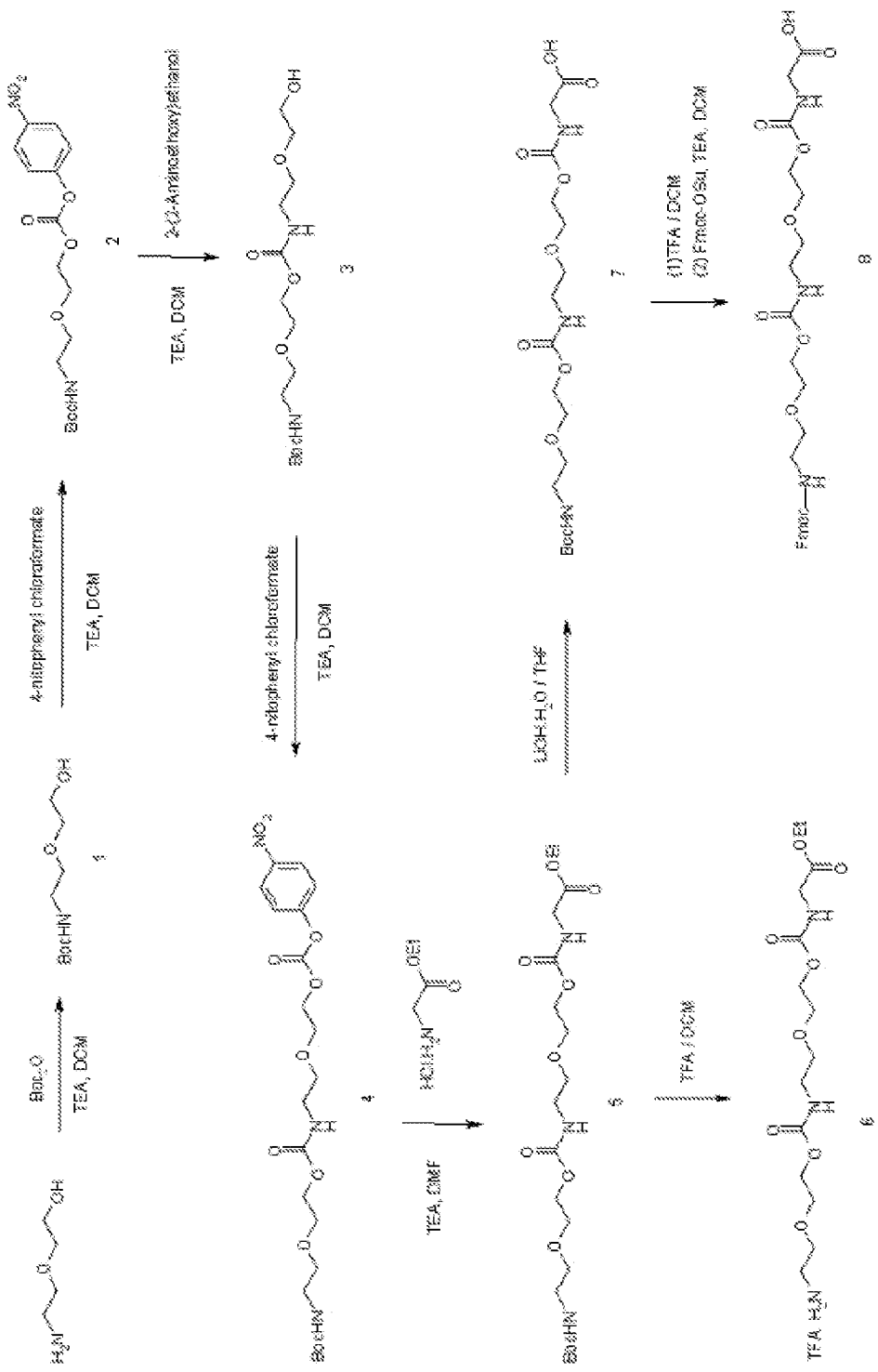
FIG. 3 shows a synthesis procedure of a linear amino acid spacer (Compound 8) prepared in Example 1.
Figure 4:
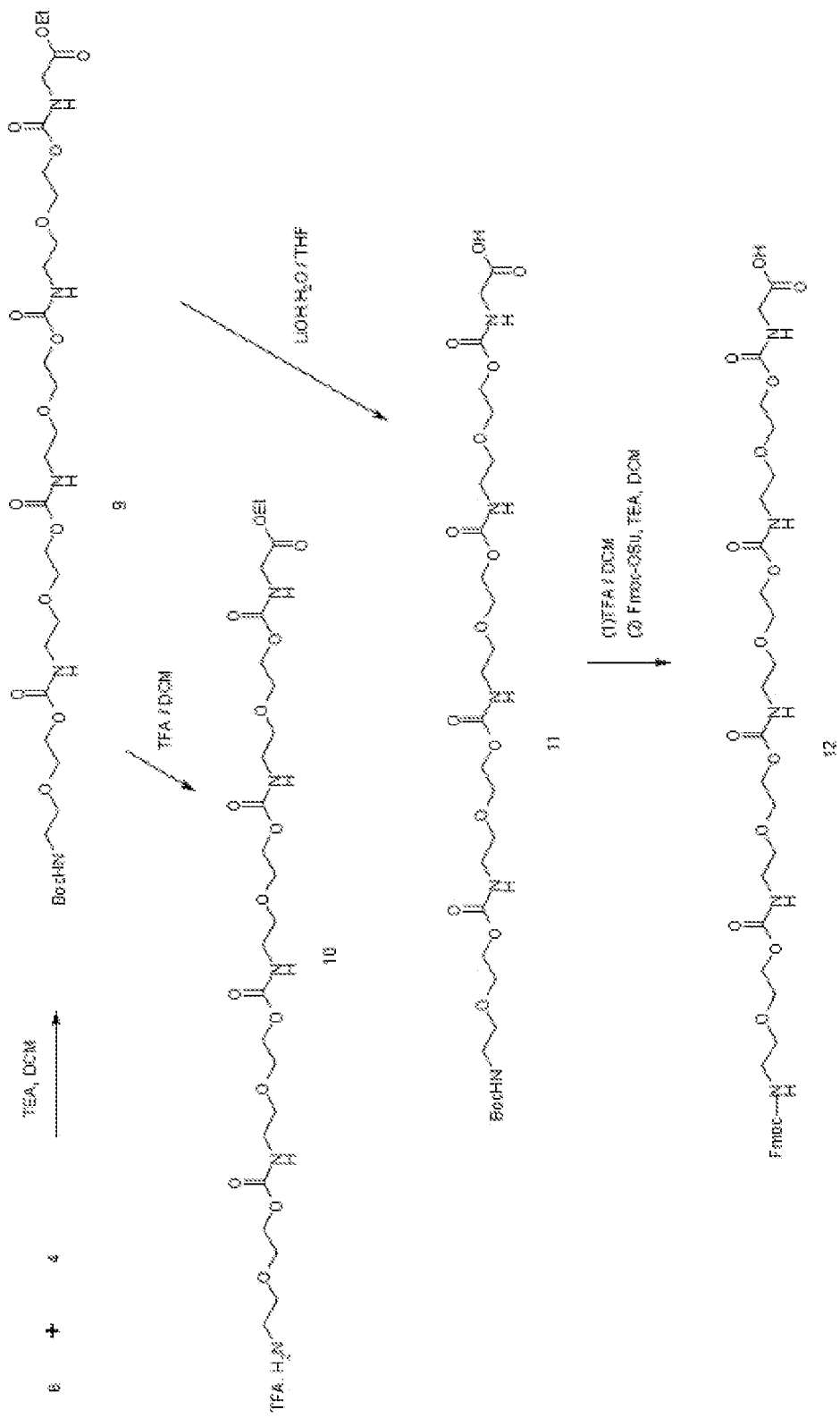
FIG. 4 shows a synthesis procedure of a linear amino acid spacer (Compound 12) prepared in Example 2.

FIGS. 2 to 4 show processes of synthesizing a PNA oligomer and a long linear amino acid spacer according to the present invention. The present invention will be described in more detail through examples. The following examples are for illustrative purposes only and not intended to limit the scope of this disclosure.

EXAMPLE 1

Synthesis of Long Linear Aamino Acid Monomer (Compound 8) [FIG. 3]

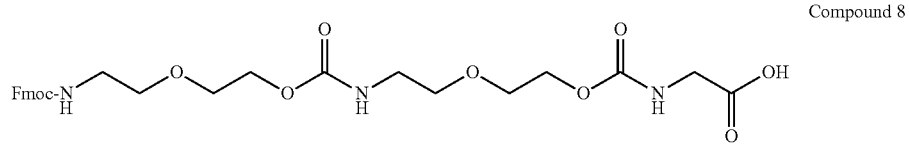

Compound 8

[1-1] Synthesis of t-butyl 2-(2-hydroxyethoxy)ethyl carbamate (Compound 1)

2-(2-Aminoethoxy)ethanol (30 g, 0.28 mol) was dissolved in dichloromethane (500 mL). After sufficiently cooling in an ice bath, t-butoxycarbonyl (Boc) anhydride (82 g, 0.36 mol, 1.3 eq) was slowly added. After sufficiently cooling for 20 minutes, followed by addition of triethylamine (40 mL, 0.28 mol, 1 eq), the mixture was stirred at room temperature for 40 minutes. Then, the reaction mixture was washed with 1 N hydrochloric acid (HCl) aqueous solution (500 mL). The organic layer was dried with magnesium sulfate ($MgSO_4$) and the solvent was removed. The target compound t-butyl 2-(2-hydroxyethoxy)ethyl carbamate (Compound 1) was yielded (56 g, 92%).

$^1$H NMR ($CDCl_3$) δ 1.44 (s, $(CH_3)_3C$—, 9H), 3.21 (q, J=5.2 Hz, —$HNCH_2CH_2$—, 2H), 3.53-3.60 (m, —$CH_2CH_2OCH_2$—, —$OCH_2$—, 4H), 3.69 (q, J=4.4 Hz, —$CH_2CH_2OH$, 2H), 4.69 (brs, —$CH_2OH$, 1H), 5.9 (brs, —$CNHCH_2$—, 1H).

[1-2] Synthesis of t-butyl 2-(2-((4-nitrophenoxy)carbonyloxy)ethoxy)ethyl carbamate (Compound 2)

t-Butyl 2-(2-hydroxyethoxy)ethyl carbamate (Compound 1, 47 g, 0.14 mol) was dissolved in dichloromethane (400 mL). After sufficiently cooling in an ice bath, 4-nitrophenyl chloroformate (33.2 g, 0.17 mol, 1.2 eq) dissolved in dichloromethane was slowly added. After sufficiently cooling for 20 minutes, followed by addition of triethylamine (39 mL, 0.28 mol, 2 eq), the mixture was stirred at room temperature for 1 hour. Then, the reaction mixture was washed 2 times with 1 N HCl aqueous solution (500 mL). The organic layer was separated and dried with magnesium sulfate. Concentration followed by purification by silica gel column chromatography yielded the target compound t-butyl 2-(2-((4-nitrophenoxy)carbonyloxy)ethyl carbamate (Compound 2, 57.8 g, 90.7%).

$^1$H NMR ($CDCl_3$) δ 1.44 (s, $(CH_3)_3C$—, 9H), 3.32 (q, J=5.2 Hz, —$HNCH_2CH_2$—, 2H), 3.56 (t, J=5.2 Hz, —$CH_2CH_2O$—, 2H), 3.67 (t, J=5.2 Hz, —$OCH_2CH_2$—, 2H), 4.25 (t, J=4.4 Hz, —$CH_2CH_2O$—, 2H), 5.2 (brs, —$CNHCH_2$—, 1H), 7.45 (d, J=6.8 Hz, Ar—H, 2H), 8.33 (d, J=6.8 Hz, Ar—H, 2H).

[1-3] Synthesis of 2-(2-(t-butoxycarbonylamino)ethoxy)ethyl 2-(2-hydroxyethoxy)ethyl carbamate (Compound 3)

t-Butyl 2-(2-((4-nitrophenoxy)carbonyloxy)ethoxy)ethyl carbamate (Compound 2, 47 g, 0.12 mol) was dissolved in dichloromethane 500 (mL). After slowly adding 2-(2-aminoethoxy)ethanol (19.3 mL, 0.18 mol, 1.5 eq), followed by addition of triethylamine (12.5 mL, 0.084 mol, 0.7 eq), the mixture was stirred at room temperature for 90 minutes. The reaction mixture washed with 1 N HCl aqueous solution (500 mL) and then 2 times with 0.5 N sodium hydroxide (NaOH) aqueous solution. The organic layer was separated and dried with magnesium sulfate. The target compound 2-(2-(t-butoxycarbonylamino)ethoxy)ethyl 2-(2-hydroxyethoxy)ethyl carbamate (Compound 3) was yielded (40 g, 92%).

$^1$H NMR ($CDCl_3$) δ 1.44 (s, $(CH_3)_3C$—, 9H), 3.32-3.46 (m, —$HNCH_2CH_2$—, 4H), 3.56-3.62 (m, —$CH_2CH_2O$—, 4H), 3.67-3.79 (m, —$OCH_2CH_2$—, 4H), 4.25 (t, J=5.2 Hz, —$CH_2CH_2O$—, 2H), 4.65 (t, J=4.4 Hz, —$CH_2CH_2OH$, 2H), 4.8 (brs, —$CH_2OH$, 1H), 4.9 (brs, —$CNHCH_2$—, 1H), 5.2 (brs, —$CNHCH_2$—, 1H).

[1-4] Synthesis of 2-(2-(t-butoxycarbonylamino)ethoxy)ethyl 2-(2-((4-nitrophenoxy)carbonyloxy)ethoxy)ethyl carbamate (Compound 4)

The target compound 2-(2-(t-butoxycarbonylamino)ethoxy)ethyl 2-(2-((4-nitrophenoxy)carbonyloxy)ethoxy)ethyl carbamate (Compound 4, 57.8 g, 91%) was prepared from 2-(2-(t-butoxycarbonylamino)ethoxy)ethyl 2-(2-hydroxyethoxy)ethyl carbamate (Compound 3, 47 g, 0.14 mol) in the same manner as [1-2].

$^1$H NMR ($CDCl_3$) δ 1.47 (s, $(CH_3)_3C$—, 9H), 3.35 (q, J=5.2 Hz, —$HNCH_2CH_2$—, 2H), 3.46 (q, J=5.2 Hz, —HN$CH_2CH_2$—, 2H), 3.58 (t, J=5.2 Hz, —$CH_2CH_2O$—, 2H), 3.64 (t, J=5.2 Hz, —$CH_2CH_2O$—, 2H), 3.69 (t, J=4.4 Hz, —$OCH_2CH_2$—, 2H), 3.81 (t, J=4.4 Hz, —$OCH_2CH_2$—, 2H), 4.27 (t, J=4.4 Hz, —$CH_2CH_2O$—, 2H), 4.48 (t, J=4.4 Hz, —$CH_2CH_2O$—, 2H), 4.97 (brs, —$CNHCH_2$—, 1H), 5.21 (brs, —$CNHCH_2$—, 1H), 7.45 (d, J=6.8 Hz, Ar—H, 2H), 8.33 (d, J=6.8 Hz, Ar—H, 2H).

[1-5] Synthesis of (2-{2-[2-(2-t-butoxycarbonylaminoethoxy)ethoxycarbonylamino]ethoxy}ethoxycarbonylamino)acetic acid ethyl ester (Compound 5)

Glycine ethyl ester (hydrochloride, 8.5 g, 0.06 mol, 1.5 eq) was dissolved in dimethylformamide (300 mL). After sequentially adding 2-(2-(t-butoxycarbonylamino)ethoxy)ethyl 2-(2-((4-nitrophenoxy)carbonyloxy)ethoxy)ethyl carbamate (Compound 4, 20 g, 0.04 mol) and triethylamine (17 mL, 0.12 mol, 3 eq), the mixture was stirred for 2 hours. Then, the reaction mixture washed 2 times with 1 N HCl aqueous solution (500 mL). The organic layer was separated, dried with magnesium sulfate, and then concentrated. Purification of the concentrate by silica gel column chromatography yielded the target compound (2-{2-[2-(2-t-butoxycarbonylaminoethoxy)ethoxycarbonylamino]ethoxy}ethoxycarbonylamino)-acetic acid ethyl ester (Compound 5, 17.5 g, 94.2%).

$^1$H NMR (CDCl$_3$) δ 1.29 (t, J=7.1 Hz, —CH$_2$CH$_3$, 3H), 1.45 (s, (CH$_3$)$_3$C—, 9H), 3.33 (q, J=5.2 Hz, —HNCH$_2$CH$_2$—, 2H), 3.38 (q, J=5.2 Hz, —HNCH$_2$CH$_2$—, 2H), 3.53-3.58 (m, —CH$_2$CH$_2$O—, 4H), 3.64-3.67 (m, —OCH$_2$CH$_2$—, 4H), 3.95 (d, J=5.7 Hz, —NHCH$_2$C—, 2H), 4.18-4.26 (m, —CH$_2$CH$_2$O—, —OCH$_2$CH$_3$, 6H), 5.04 (brs, —CNHCH$_2$—, 1H), 5.50 (m, —CNHCH$_2$—, 2H).

[1-6] Synthesis of (2-{2-[2-(2-t-butoxycarbonylaminoethoxy)ethoxycarbonylamino]ethoxy}ethoxycarbonylamino)acetic acid (Compound 7)

(2-{2-[2-(2-t-Butoxycarbonylaminoethoxy)ethoxycarbonylamino]ethoxy}ethoxycarbonylamino)acetic acid ethyl ester (Compound 5, 12.2 g, 0.026 mol) was dissolved in tetrahydrofuran (THF, 150 mL) and then stirred. After slowly adding 2 N lithium hydroxide (LiOH) aqueous solution (40 mL), the mixture was stirred at room temperature for 40 minutes. After removing THF from the reaction mixture, 1 N HCl was slowly added for acidification. After extracting 3 times with dichloromethane, the organic layer was separated, dried with magnesium sulfate, and then concentrated. The target compound (2-{2-[2-(2-t-butoxycarbonylaminoethoxy)ethoxycarbonylamino]ethoxy}ethoxycarbonylamino)acetic acid (Compound 7, 11 g, 90.1%) was yielded.

$^1$H NMR (CDCl$_3$) δ 1.45 (s, (CH$_3$)$_3$C—, 9H), 3.31 (q, —HNCH$_2$CH$_2$—, J=5.2 Hz, 2H), 3.37 (q, —HNCH$_2$CH$_2$—, J=5.2 Hz, 2H), 3.55-3.58 (m, —CH$_2$CH$_2$O—, 4H), 3.66-3.68 (m, —OCH$_2$CH$_2$—, 4H), 3.98 (d, —NHCH$_2$C—, J=5.7 Hz, 2H), 4.25-4.27 (m, —CH$_2$CH$_2$O—, 4H), 5.14-5.60 (m, —CNHCH$_2$—, 3H).

[1-7] Synthesis of [2-(2-{2-[2-((9H-fluoren-9-ylmethoxy)carbonylamino)ethoxy]ethoxycarbonylamino}ethoxy)ethoxycarbonylamino]acetic acid (Compound 8)

(2-{2-[2-(2-t-Butoxycarbonylaminoethoxy)ethoxycarbonylamino]ethoxy}ethoxycarbonylamino)acetic acid (Compound 7, 7.1 g, 0.016 mol) was dissolved in dichloromethane (80 mL) and then stirred. After slowly adding trifluoroacetic acid (80 mL), the mixture was stirred at room temperature for 30 minutes. After removing the solvent and washing 2 times with diethyl ether, followed by drying, the dried compound was dissolved in dichloromethane (80 mL). After sufficiently cooling in an ice bath, triethylamine (22 mL, 0.16 mol, 10 eq) was slowly added for neutralization. After adding N-succinimidyl 9H-fluoren-9-ylmethyl carbonate (Fmoc-OSu, 6.6 g, 0.019 mol, 1.2 eq), the mixture was stirred for 2 hours at room temperature. Then, the reaction mixture was washed 2 times with 1 N HCl aqueous solution. The organic layer was separated, dried with magnesium sulfate, and then concentrated. Purification by silica gel column chromatography yielded the target compound [2-(2-{2-[2-((9H-fluoren-9-ylmethoxy)carbonylamino)ethoxy]ethoxycarbonylamino}ethoxy)ethoxycarbonylamino]acetic acid (Compound 8, 6.8 g, 76%).

$^1$H NMR (CDCl$_3$) δ 3.33-3.35 (m, —HNCH$_2$CH$_2$—, 4H), 3.46-3.63 (m, CH$_2$CH$_2$O—, —OCH$_2$CH$_2$, 8H), 3.96 (d, J=5.7 Hz, —NHCH$_2$C—, 2H), 4.21-4.23 (m, —CH$_2$CH$_2$O—, —CHCH$_2$O—, 5H), 4.40 (d, J=6.8 Hz, —CHCH$_2$O—, 2H), 5.55-5.66 (m, —CNHCH$_2$—, 3H), 7.30 (t, J=7.3 Hz, Ar—H, 2H), 7.39 (t, J=7.3 Hz, Ar—H, 2H), 7.60 (d, J=7.3 Hz, Ar—H, 2H), 7.76 (d, J=7.3 Hz, Ar—H, 2H); MALDI-TOF MS for C$_{27}$H$_{33}$N$_3$O$_{10}$ [M+H$^+$]: calcd 599.58, found 590.62.

EXAMPLE 2

Synthesis of Long Linear Amino Acid Monomer (Compound 12) [FIG. 4]

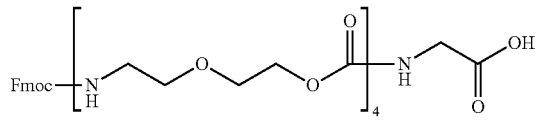

Compound 12

[2-1] Synthesis of ethyl 38,38-dimethyl-4,12,20,28,36-pentaoxo-5,8,13,16,21,24,29,32,37-nonaoxa-3,11,19,27,65-pentaazanonatriacontan-1-oate (Compound 9)

(2-{2-[2-(2-t-Butoxycarbonylaminoethoxy)ethoxycarbonylamino]ethoxy}ethoxycarbonylamino acetic acid ethyl ester (Compound 5, 13.2 g, 0.03 mol, 1 eq) was dissolved in dichloromethane (100 mL) and then stirred. After slowly adding trifluoroacetic acid (150 mL), the mixture was stirred at room temperature for 30 minutes. After removing the solvent, washing 2 times with diethyl ether followed by drying yielded trifluoroacetate of (2-{2-[2-(aminoethoxy)ethoxycarbonylamino]ethoxy}ethoxycarbonylamino)acetic acid ethyl ester (Compound 6, 14.3 g, 99.4%). The trifluoroacetate of (2-{2-[2-(aminoethoxy)ethoxycarbonylamino]ethoxy}ethoxycarbonylamino)acetic acid ethyl ester (Compound 6, 14.1 g, 0.029 mol, 1.5 eq) was dissolved in dichloromethane (200 mL). After sufficiently cooling in an ice bath, triethylamine (28 mL, 0.2 mol, 10 eq) was slowly added for neutralization. Then, previously synthesized 2-(2-(t-butoxycarbonylamino)ethoxy)ethyl 2-(2-((4-nitrophenoxy)carbonyloxy)ethoxy)ethyl carbamate (Compound 4, 10 g, 0.02 mol, 1 eq) was added. After slowly adding triethylamine (5.6 mL, 0.04 mol, 2 eq), the mixture was stirred at room temperature for 3 hours. Then, the reaction mixture was washed 3 times with 1 N HCl aqueous solution (250 mL). The organic layer was separated, dried with magnesium sulfate, and then concentrated. Purification by silica gel column chromatography yielded the target compound ethyl 38,38-dimethyl-4,12,20,28,36-pentaoxo-5,8,13,16,21,24,29,32,37-nonaoxa-3,11,19,27,65-pentaazanonatriacontan-1-oate (Compound 9, 10.2 g, 74%).

$^1$H NMR (CDCl$_3$) δ 1.29 (t, J=7.1 Hz, —CH$_2$CH$_3$, 3H), 1.44 (s, (CH$_3$)$_3$C—, 9H), 3.30-3.40 (m, —HNCH$_2$CH$_2$—, 8H), 3.52-3.58 (m, —CH$_2$CH$_2$O—, 8H), 3.65-3.66 (m, —OCH$_2$CH$_2$—, 8H), 3.95 (d, J=5.7 Hz, —NHCH$_2$C—, 2H), 4.18-4.26 (m, —CH$_2$CH$_2$O—, —OCH$_2$CH$_3$, 10H), 5.07 (brs, —CNHCH$_2$—, 1H), 5.42-5.60 (m, —CNHCH$_2$—, 4H).

[2-2] Synthesis of 38,38-dimethyl-4,12,20,28,36-pentaoxo-5,8,13,16,21,24,29,32,37-nonaoxa-3,11,19,27,35-pentaaza-1-nonatriacontanoic acid (Compound 11)

Ethyl 38,38-dimethyl-4,12,20,28,36-pentaoxo-5,8,13,16,21,24,29,32,37-nonaoxa-3,11,19,27,65-pentaazanonatriacontan-1-oate (Compound 9, 17 g, 0.025 mol) was dissolved in THF (170 mL) and then stirred. After slowly adding 2 N lithium hydroxide aqueous solution (55 mL), the mixture was stirred at room temperature for 40 minutes. After removing THF from the reaction mixture, 1 N HCl aqueous solution was slowly added for acidification. After extracting 3 times with dichloromethane, the organic layer was separated, dried with magnesium sulfate, and the concentrated. The target compound 38,38-dimethyl-4,12,20,28,36-pentaoxo-5,8,13,16,21,24,29,32,37-nonaoxa-3,11,19,27,35-pentaaza-1-nonatriacontanoic acid (Compound 11, 15.5 g, 98.3%) was yielded.

$^1$H NMR (CDCl$_3$) δ 1.44 (s, (CH$_3$)$_3$C—, 9H), 3.30-3.40 (m, —HNCH$_2$CH$_2$—, 8H), 3.52-3.69 (m, —CH$_2$CH$_2$O—, —OCH$_2$CH$_2$—, 16H), 3.95 (d, J=5.7 Hz, —NHCH$_2$C—, 2H), 4.17-4.24 (m, —CH$_2$CH$_2$O—, 8H), 5.21-5.70 (m, —CNHCH$_2$—, 5H).

[2-3] Synthesis of 1-(9H-fluoren-9-yl)-3,11,19,27,35-pentaoxo-2,7,10,15,18,23,26,31,34-nonaoxa-4,12,20,28,36-pentaaza-28-octatriacontanoic acid (Compound 12)

38,38-Dimethyl-4,12,20,28,36-pentaoxo-5,8,13,16,21,24,29,32,37-nonaoxa-3,11,19,27,35-pentaaza-1-nonatriacontanoic acid (Compound 11, 10 g, 0.015 mol) was dissolved in dichloromethane (100 mL) and then stirred. After slowly adding trifluoroacetic acid (150 mL), the mixture was stirred at room temperature for 30 minutes. After removing the solvent, followed by washing 2 times with diethyl ether and drying, the dried compound was dissolved in dichloromethane (100 mL) After sufficiently cooling in an ice bath, triethylamine (20 mL, 0.15 mol, 10 eq) was slowly added for neutralization. After adding N-succinimidyl 9H-fluoren-9-ylmethyl carbonate, the mixture was stirred for 2 hours at room temperature. After washing the reaction mixture 2 times with 1 N HCl aqueous solution, the organic layer was separated, dried with magnesium sulfate, and then concentrated. Purification by silica gel column chromatography yielded the target compound l-(9H-fluoren-9-yl)-3,11,19,27,35-pentaoxo-2,7,10,15,18,23,26,31,34-nonaoxa-4,12,20,28,36-pentaaza-28-octatriacontanoic acid (Compound 12, 9.1 g, 78%).

$^1$H NMR (CDCl$_3$) δ 3.33-3.45 (m, —HNCH$_2$CH$_2$—, 8H), 3.46-3.63 (m, —CH$_2$CH$_2$O—, —OCH$_2$CH$_2$—, 16H), 3.96 (d, J=5.7 Hz, —NHCH$_2$C—, 2H), 4.19-4.23 (m, —CH$_2$CH$_2$O—, —CHCH$_2$—, 9H), 4.40 (d, J=6.8 Hz, —CHCH$_2$O, 2H), 5.56-5.80 (m, —CNHCH$_2$—, 5H), 7.29 (t, J=7.3 Hz, Ar—H, 2H), 7.36 (t, J=7.3 Hz, Ar—H, 2H), 7.57 (d, J=7.3 Hz, Ar—H, 2H), 7.73 (d, J=7.3 Hz, Ar—H, 2H); MALDI-TOF MS for C$_{37}$H$_{51}$N$_5$O$_{16}$ [M+H$^+$]: calcd 821.84, found 822.96.

EXAMPLE 3

Figure 5:
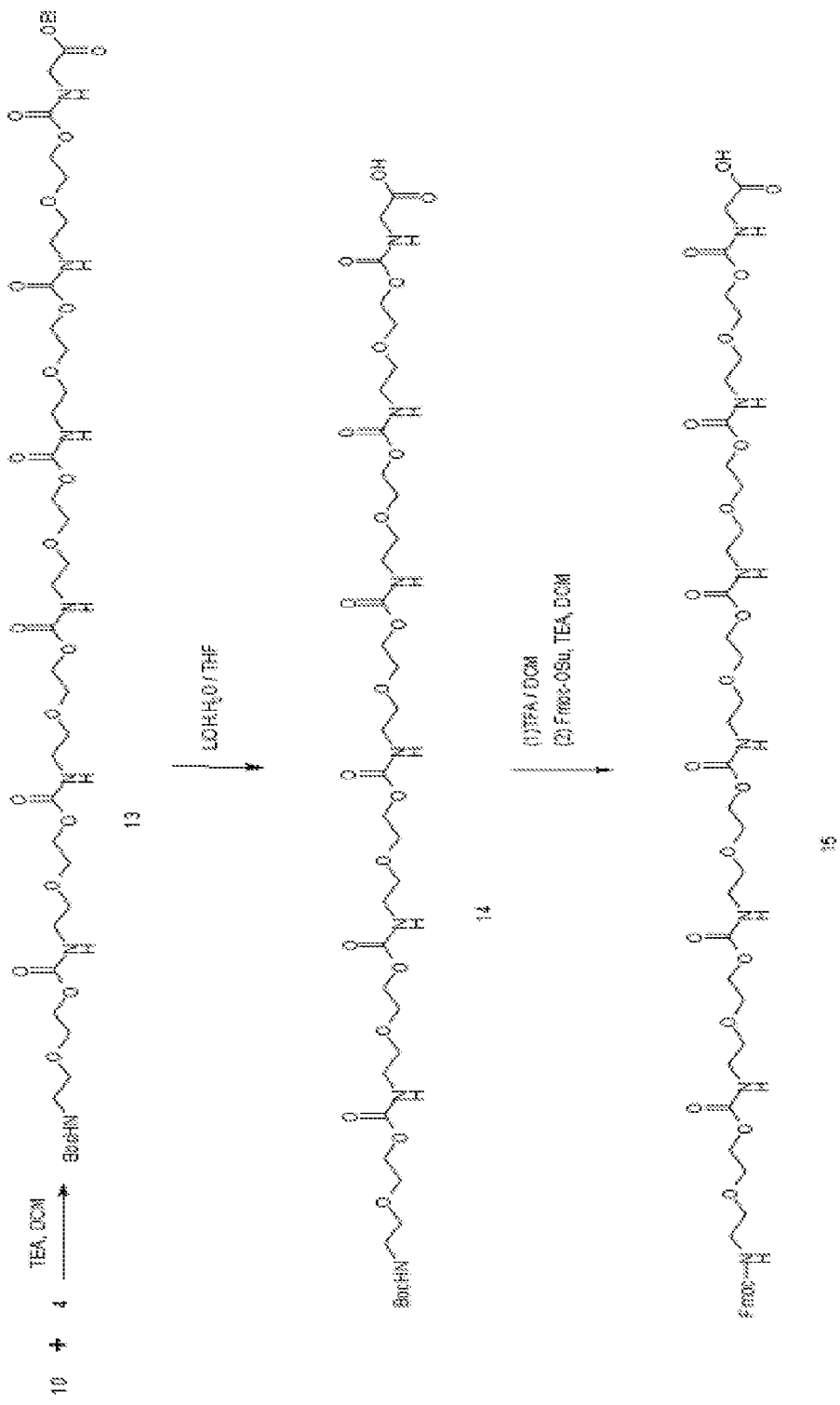
FIG. 5 shows a synthesis procedure of a linear amino acid spacer (Compound 15) prepared in Example 3.

Synthesis of Long Linear Amino Acid Monomer (Compound 15) [FIG. 5]

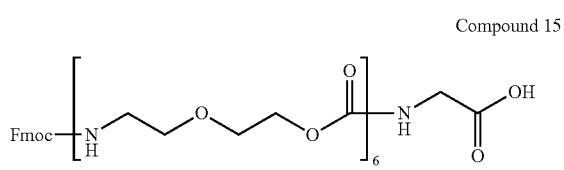

Compound 15

[3-1] Synthesis of ethyl 54,54-dimethyl-4,12,20,28,36,44,52-heptaoxo-5,8,13,16,21,24,29,32,37,40,45,48,53-tridecaoxa-3,11,19,27,35,43,51-heptaazapentapentacontan-1-oate (Compound 13)

Ethyl 38,38-dimethyl-4,12,20,28,36-pentaoxo-5,8,13,16,21,24,29,32,37-nonaoxa-3,11,19,27,65-pentaazanonatriacontan-1-oate (Compound 9, 2.8 g, 0.0039 mol, 1 eq) was dissolved in dichloromethane (30 mL) and then stirred. After slowly adding trifluoroacetic acid (30 mL), the mixture was stirred at room temperature for 30 minutes. After removing the solvent, followed by washing 2 times with diethyl ether and drying, a trifluoroacetate of (2-(2-(2-(2-(2-(2-(2-(amino-ethoxy)ethoxycarbonylamino)ethoxy)ethoxycarbonylamino)ethoxy)ethoxycarbonylamino)ethoxy)ethoxycarbonylamino)acetic acid ethyl ester (Compound 10, 3.0 g, 99.6%) was obtained. The trifluoroacetate of (2-(2-(2-(2-(2-(2-(2-(aminoethoxy)ethoxycarbonylamino)ethoxy)ethoxycarbonylamino)ethoxy)ethoxycarbonylamino)ethoxy)ethoxycarbonylamino)acetic acid ethyl ester (Compound 10, 3.0 g, 0.0039 mol, 1.2 eq) was dissolved in dichloromethane (30 mL). After sufficiently cooling in an ice bath, triethylamine (5.6 mL, 0.04 mol, 10 eq) was slowly added for neutralization. Previously synthesized 2-(2-(t-butoxycarbonylamino)ethoxy)ethyl 2-(2-((4-nitrophenoxy)carbonyloxy)ethoxy)ethyl carbamate (Compound 4, 1.7 g, 0.0033 mol, 1 eq) was added. Then, after slowly adding triethylamine (2.7 mL, 0.02 mol, 5 eq), the mixture was stirred at room temperature for 12 hours. Then, the reaction mixture was washed 3 times with 1 N HCl aqueous solution. The organic layer was separated, dried with magnesium sulfate, and then concentrated. Purification by silica gel column chromatography yielded the target compound ethyl 54,54-dimethyl-4,12,20,28,36,44,52-heptaoxo-5,8,13,16,21,24,29,32,37,40,45,48,53-tridecaoxa-3,11,19,27,35,43,51-heptaazapentapentacontan-1-oate (Compound 13, 2.5 g, 73%).

$^1$H NMR (CDCl$_3$) δ 1.28 (t, —CH$_2$CH$_3$, J=7.1 Hz, 3H), 1.45 (s, (CH$_3$)$_3$C—, 9H), 3.30-3.40 (m, —HNCH$_2$CH$_2$—, 12H), 3.52-3.58 (m, —CH$_2$CH$_2$O—, 12H), 3.65-3.67 (m, —OCH$_2$CH$_2$—, 12H), 3.95 (d, J=5.7 Hz, —NHCH$_2$C—, 2H), 4.17-4.26 (m, —CH$_2$CH$_2$O—, —OCH$_2$CH$_3$, 14H), 5.09 (brs, —CNHCH$_2$—, 1H), 5.50-5.62 (m, —CNHCH$_2$—, 6H).

[3-2] Synthesis of 54,54-dimethyl-4,12,20,28,36,44,52-heptaoxo-5,8,13,16,21,24,29,32,37,40,45,48,53-tridecaoxa-3,11,19,27,35,43,51-heptaaza-1-pentapentacontanoic acid (Compound 14)

Ethyl 54,54-dimethyl-4,12,20,28,36,44,52-heptaoxo-5,8,13,16,21,24,29,32,37,40,45,48,53-tridecaoxa-3,11,19,27,35,43,51-heptaazapentapentacontan-1-oate (Compound 13, 2.4 g, 0.0025 mol) was dissolved in THF (30 mL) and then stirred. After slowly adding 2 N lithium hydroxide aqueous solution (8 mL), the mixture was stirred at room temperature for 40 minutes. After removing THF from the reaction mixture, 1 N HCl aqueous solution was slowly added for acidification. After extracting 3 times with dichloromethane, the organic layer was separated, dried with magnesium sulfate, and then concentrated. The target compound 54,54-dimethyl-4,12,20,28,36,44,52-heptaoxo-5,8,13,16,21,24,29,32,37,40,45,48,53-tridecaoxa-3,11,19,27,35,43,51-heptaaza-1-pentapentacontanoic acid (Compound 14, 2.3 g, 99.1%) was yielded.

$^1$H NMR (CDCl$_3$) δ 1.48 (s, (CH$_3$)$_3$C—, 9H), 3.36-3.37 (m, —HNCH$_2$CH$_2$—, 12H), 3.48-3.56 (m, —CH$_2$CH$_2$O—, 12H), 3.65-3.67 (m, —OCH$_2$CH$_2$—, 12H), 3.95 (d, J=5.7 Hz, —NHCH$_2$C—, 2H), 4.17-4.24 (m, —CH$_2$CH$_2$O—, 12H), 5.13 (brs, —CNHCH$_2$—, 1H), 5.53-5.73 (m, —CNHCH$_2$—, 6H).

[3-3] Synthesis of 1-(9H-fluoren-9-yl)-3,11,19,27, 35,43,51-heptaoxo-2,7,10,15,18,23,26,31,34,39,42, 47,50-tridecaoxa-4,12,20,28,36,44,52-heptaaza-54-tetrapentacontanoic acid (Compound 15)

54,54-Dimethyl-4,12,20,28,36,44,52-heptaoxo-5,8,13, 16,21,24,29,32,37,40,45,48,53-tridecaoxa-3,11,19,27,35, 43,51-heptaaza-1-pentapentacontanoic acid (Compound 14, 2.3 g, 0.0024 mol) was dissolved in dichloromethane (30 mL) and then stirred. After slowly adding trifluoroacetic acid (30 mL), the mixture was stirred at room temperature for minutes. After removing the solvent, followed by washing 2 times with diethyl ether and drying, the dried compound was dissolved in dichloromethane (30 mL). After sufficiently cooling in an ice bath, triethylamine (3.3 mL, 0.024 mol, 10 eq) was slowly added for neutralization. After adding N-succinimidyl 9H-fluoren-9-ylmethyl carbonate (Fmoc-OSu, 1.7 g, 0.0048 mol, 2 eq), the mixture was stirred for 3 hours at room temperature. After washing the reaction mixture 2 times 1 N HCl aqueous solution, the organic layer was separated, dried with magnesium sulfate, and then concentrated. Purification by silica gel column chromatography yielded the target compound1-(9H-fluoren-9-yl)-3,11,19,27,35,43,51-heptaoxo-2, 7,10,15,18,23,26,31,34,39,42,47,50-tridecaoxa-4,12,20,28, 36,44,52-heptaaza-54-tetrapentacontanoic acid (Compound 15, 1.8 g, 69%).

$^1$H NMR (CDCl$_3$) δ 3.34-3.36 (m, —HNCH$_2$CH$_2$—, 12H), 3.54-3.63 (m, —CH$_2$CH$_2$O—, —OCH$_2$CH$_2$—, 24H), 3.95 (d, J=5.7 Hz, —NHCH$_2$C—, 2H), 4.17-4.24 (m, —CH$_2$CH$_2$O—, —CHCH$_2$—, 13H), 4.40 (d, J=6.8 Hz, —CHCH$_2$O, 2H), 5.56-5.83 (m, —CNHCH$_2$—, 7H), 7.31 (t, J=7.3 Hz, Ar—H, 2H), 7.40 (t, J=7.3 Hz, Ar—H, 2H), 7.60 (d, J=7.3 Hz, Ar—H, 2H), 7.76 (d, Ar—H, J=7.3 Hz, 2H); MALDI-TOF MS for C$_{47}$H$_{69}$N$_7$O$_{22}$ [M+H$^+$]: calcd 1084.11, found 1085.30.

EXAMPLES 4-8

Synthesis of PNA Probe having Long Linear Chain Amino Acid

A PNA oligomer was synthesized by solid-phase synthesis from a PNA monomer protected with a benzothiazolesulfonyl (Bts) group and a functionalized resin according to the method of Korean Patent Publication No. 2007-0040420. The PNA was used in the next reaction as attached to the resin.

1) To the PNA attached to the resin, 1 M lithium chloride (LiCl) in dimethylformamide solution and methoxybenzenethiol were added at a proportion of 7.7/1 (v/v). After shaking at room temperature for 1 minute, (70%, vol %) diisopropylethylamine in methoxybenzenethiol was added. After shaking at 40° C. for 10 minutes to remove the Bts amine protecting group at the N-terminus of the PNA, the mixture was washed 5 times with dimethylformamide.

2) Amino acid (Compound 8, 12 or 15 prepared in Examples 1 to 3, 5 eq), N-hydroxybenzotriazole (5 eq), diisopropylcarbodiimide (10 eq) and dimethylformamide were added, based on the resin. After shaking at 40° C. for 1 hour, the mixture was washed 5 times with dimethylformamide.

3) After adding dimethylformamide including 5% acetic anhydride and 6% lutidine and shaking well at room temperature for 5 minutes, the mixture was washed 3 times with dimethylformamide.

4) After treating with 10% piperidine in dimethylformamide solution at room temperature for 20 minutes to remove the Fmoc amine protecting group at the N-terminus, the mixture was washed 5 times with dimethylformamide.

5) The steps 2) to 4) were repeated as desired to synthesize a PNA having a long linear chain amino acid.

6) The steps 2) to 4) were repeated twice for the PNA oligomer with the spacer attached, which was synthesized in the step 5), using FmocLys(Fmoc)-OH in order to synthesize a PNA having a long linear chain amino acid with an immobilization linker attached.

7) The PNA probe attached to the resin, which was synthesized in the step 6), was treated with m-cresol/trifluoroacetic acid (1/4, v/v) solution for 2 hours to detach the PNA probe from the resin. Then, diethyl ether was added to precipitate the PNA probe.

8) The precipitated PNA was filtered, washed with diethyl ether, and purified by HPLC. PNA compounds conjugated with amino acid spacers were obtained.

TABLE 1

| Example No. | Probe No. | Probe name | Base sequence (N to C) | Spacer structure and length |
|---|---|---|---|---|
| Example 4 | 1 | PNA 204t-18sp | tcatccatataactg | 19 atoms |
|  | 2 | PNA 204c-18sp | tcatccacataactg |  |
|  | 3 | PNA 204g-18sp | tcatccagataactg |  |
|  | 4 | PNA 204a-18sp | tcatccaaataactg |  |
| Example 5 | 5 | PNA 204t-38sp | tcatccatataactg | 38 atoms |
|  | 6 | PNA 204c-38sp | tcatccacataactg |  |
|  | 7 | PNA 204g-38sp | tcatccagataactg |  |
|  | 8 | PNA 204a-38sp | tcatccaaataactg |  |

TABLE 1-continued

| Example No. | Probe No. | Probe name | Base sequence (N to C) | Spacer structure and length |
|---|---|---|---|---|
| Example 6 | 9 | PNA 204t-70sp | tcatccatataactg | 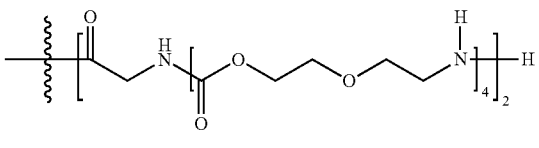<br>70 atoms |
| | 10 | PNA 204c-70sp | tcatccacataactg | |
| | 11 | PNA 204g-70sp | tcatccagataactg | |
| | 12 | PNA 204a-70sp | tcatccaaataactg | |
| Example 7 | 13 | PNA 204t-102sp | tcatccatataactg | 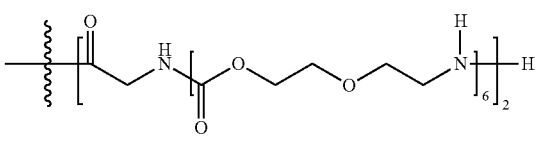<br>102 atoms |
| | 14 | PNA 204c-102sp | tcatccacataactg | |
| | 15 | PNA 204g-102sp | tcatccagataactg | |
| | 16 | PNA 204a-102sp | tcatccaaataactg | |
| Example 8 | 17 | PNA 204t-153sp | tcatccatataactg | 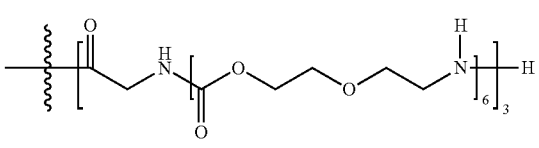<br>153 atoms |
| | 18 | PNA 204c-153sp | tcatccacataactg | |
| | 19 | PNA 204g-153sp | tcatccagataactg | |
| | 20 | PNA 204a-153sp | tcatccaaataactg | |

EXAMPLE 9

Obtainment of Recombinant HBV Clones

*E. coli* JM109 (Stratagene, USA) was transformed to obtain a large amount of DNAs of wild type human hepatitis B virus (HBV) and lamivudine-resistant mutant HBV. The DNAs were sequenced to confirm the genotypes of the wild type and the mutant HBV.

EXAMPLE 10

Preparation of Target DNA

DNAs isolated from a clinical sample and the DNAs of wild type HBV and lamivudine-resistant mutant HBV obtained in Example 9 were amplified by polymerase chain reaction (PCR).

Biotinylated primers described in Table 2 were used for the PCR. Primary PCR product was used as template DNA. The DNAs were amplified under the following conditions:

Treatment with template DNA solution (50 ng/μL, 1 μL), sense primer (10 pmol/μL, 1.25 μL), antisense primer (10 pmol/μL, 0.75 μL), dNTP (10 mM, 1 μL), 10× Taq buffer (containing MgCl$_2$, 5 μL), Taq (1 unit) and distilled water (30.8 μL) at 94° C. for 4 minutes, followed by 30 cycles of 1 minute at 94° C., 1 minute at 58° C. and 1 minute at 72° C.

Figure 7:
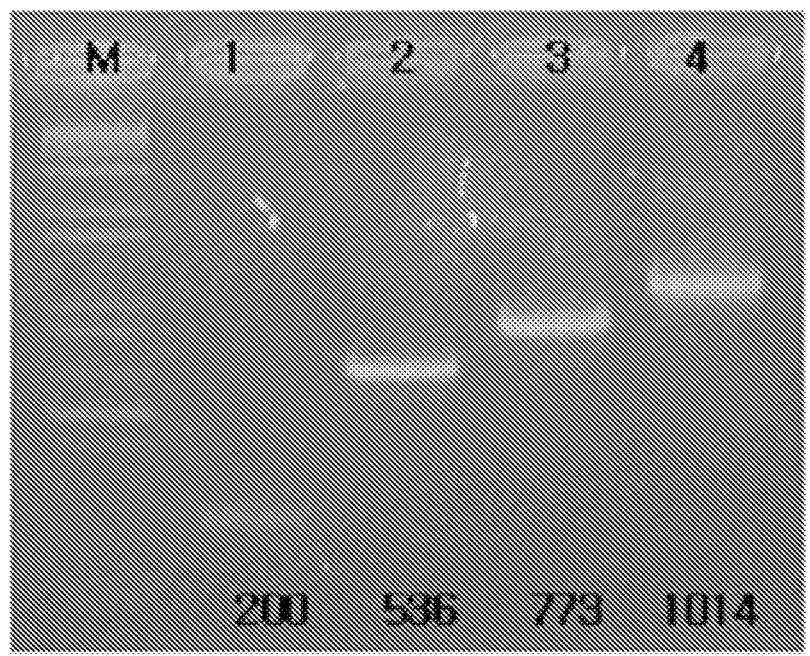
FIG. 7 shows an electrophoresis result of DNAs amplified by PCR using primers of Example 10 [M: 1 kb+ladder, 1:200 bp target DNA, 2:536 bp target DNA, 3: 773 bp target DNA, 4: 1014 bp target DNA].

Reaction product (200 bp, 536 bp, 773 bp and 1014 bp; DNA base sequences are shown in FIG. 6; 5 μL) was added to a gel loading buffer (1 μL). After electrophoresis on 1.5% agarose gel, followed by staining with 1 μg/mL ethidium bromide (EtBr), product was confirmed using a UV transilluminator. The electrophoresis result is shown in FIG. 7.

TABLE 2

| | Primer base sequence (5' → 3') | PCR product size (bp) |
|---|---|---|
| HBV 1-F Sense (SEQ ID NO: 1) | cca tca tct tgg gct ttc gc | 200 |
| HBV 1-R Antisense (SEQ ID NO: 2) | caa aag aaa attaggt aac agc ggt a | |
| HBV 2-F Sense (SEQ ID NO: 3) | gtg ctg caa ggc gat taa gt | 536 |
| HBV 2-R Antisense (SEQ ID NO: 4) | att agg cac ccc agg ctt ta | |
| HBV 3-F Sense (SEQ ID NO: 5) | gtc cat tcg cca ttc agg | 773 |
| HBV 3-R Antisense (SEQ ID NO: 6) | gag tca gtg agc gag gaa gc | |
| HBV 4-F Sense (SEQ ID NO: 7) | agg gaa gaa agc gaa agg ag | 1014 |
| HBV 4-R Antisense (SEQ ID NO: 8) | ttt acg gtt cct ggc ctt tt | |

EXAMPLE 11

Manufacture of PNA Chip

The purified PNA oligomer of Examples 4 to 8 (Table 1) was diluted to 50 mM in a spotting buffer. After spotting the PNA oligomer on a glass substrate functionalized with an epoxy group, it was allowed to stand at room temperature and 75% humidity for 4 hours. After adding dimethylformamide, the substrate was ultrasonically washed for 15 minutes. After adding 0.1 M succinic anhydride in dimethylformamide, unreacted amine group was removed at 40° C. for 2 hours. After removing the reaction solution, the substrate was ultrasonically washed for 15 minutes with dimethylformamide and then with triply distilled water. Then, after adding 100 mM Tris buffer (Tris-HCl) containing 0.1 M ethanolamine, remaining epoxy group of the solid surface was deactivated. The glass substrate was ultrasonically washed 2 times, each for 15 minutes with triply distilled water, treated with boiling water for 5 minutes, washed for 5 minutes with triply distilled water, and then dried. Then, a silicon reactor designed to contain 100 μL of hybridization solution was adhered on the glass substrate.

EXAMPLE 12

Hybridization with Target DNA on PNA Chip

Figure 8:
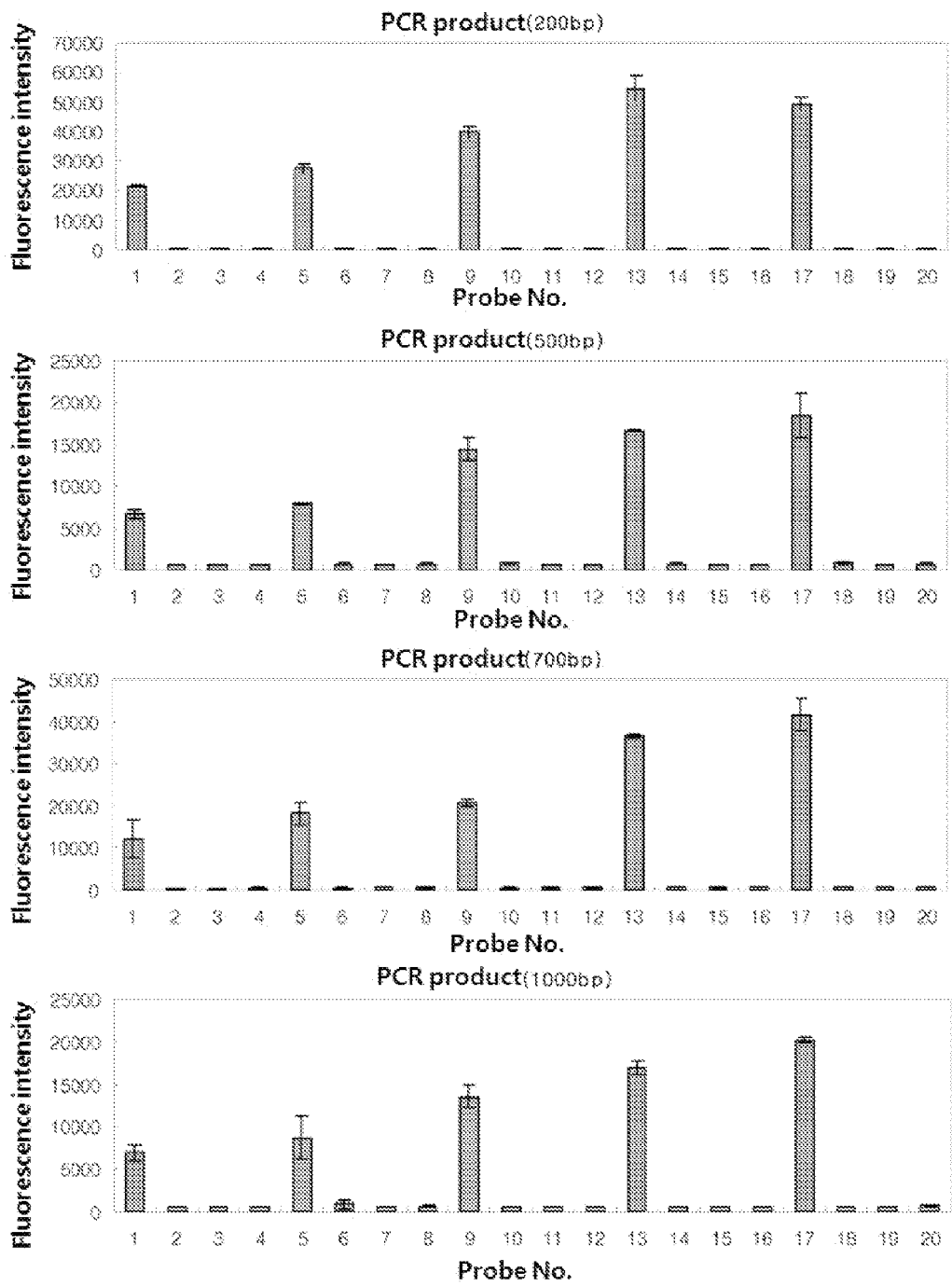
FIG. 8 compares sensitivity and specificity of signals obtained by hybridization of PCR products in Example 12 to PNA chips on which PNA probes having spacers with different lengths are immobilized.
Figure 9:
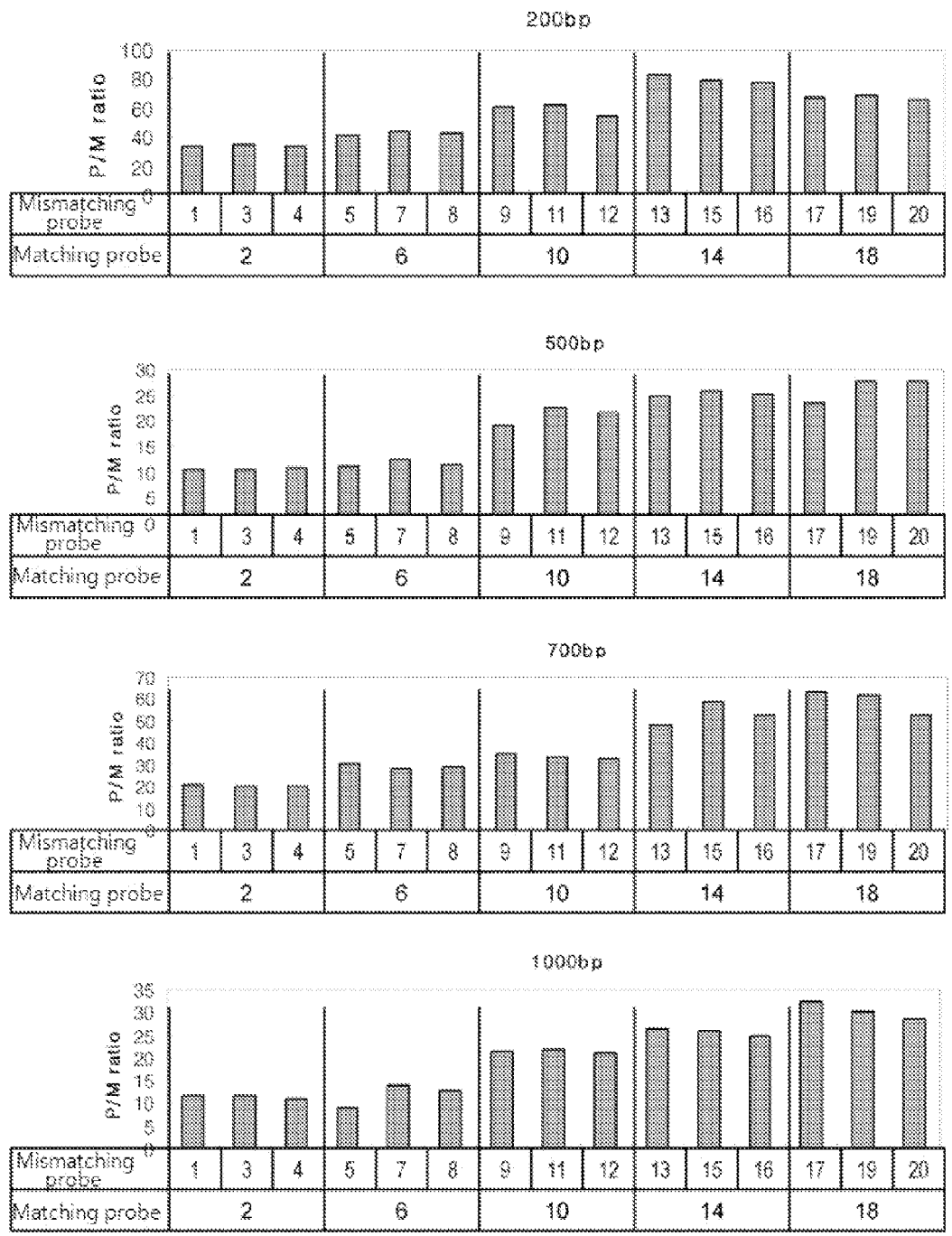
FIG. 9 compares specificity [perfect match /mismatch (P/M) signal ratio] of the signals of FIG. 8 according to the size of the PCR products.

The biotinylated PCR product (5 μL) was added to a hybridization buffer (100 μL). Streptavidin-Cy5 was added to induce fluorescence reaction. The hybridization mixture solution (100 μL) was injected through a hole of the silicon reactor prepared in Example 11, and was allowed to react at 40° C. for 2 hours. After the reaction, the glass substrate was washed 2 times with a washing buffer at room temperature for 5 minutes, and then dried. The image of the glass substrate was analyzed using a fluorescence scanner (Genepix 4000B, Exon, USA). The result is shown in FIG. 8. FIG. 9 compares specificity [perfect match/mismatch (P/M) signal ratio] of the signals of FIG. 8 according to the size of the PCR products.

FIG. 8 compares intensities of specific signals depending on the PCR product size and spacer length. For the individual PCR products (200, 500, 700 and 1000 bp), intensities of the specific signals increased when the spacer was longer.

FIG. 9 shows resolution of specific and nonspecific signals depending on the spacer length. For the 200 bp and 500 bp PCR products, P/M ratio was higher for the 38 atom spacer than the 19 atom spacer, and P/M ratio was higher for the 70 atom spacer than the 38 atom spacer. Further, P/M ratio was higher for the 102 atom spacer than the 70 atom spacer. There was no significant difference between the P/M ratio of the 102 atom and 153 atom spacers.

For the 700 bp and 1000 bp PCR products, P/M ratio was higher for the 38 atom spacer than the 19 atom spacer, and P/M ratio was higher for the 70 atom spacer than the 38 atom spacer. Further, P/M ratio was higher for the 102 atom spacer than the 70 atom spacer. And, P/M ratio was higher for the 153 atom spacer than the 102 atom spacer.

Industrial Applicability

As described above, the PNA conjugated with an amino acid spacer according to the present invention may be conjugated with one or more long linear chain amino acid monomer(s) having a plurality of alkylene glycols at the amine (N)-terminus of PNA to control the spacer length.

Further, the length of the alkylene glycols linked via carbamate may be regulated through a process of protection of an amine group of a precursor having the amine group and an alcohol group at either end, conversion of the alcohol group into an activated carbonate group, synthesis of carbamate, and conversion to carbonate.

Since the PNA conjugated with an amino acid spacer according to the present invention maintains a sufficient distance between the PNA oligomer and a support during the manufacture of a PNA chip, because of the long linear chain amino acid spacer, it provides significantly improved specificity and sensitivity of target gene detection.

The PNA conjugated with an amino acid spacer oligomer according to the present invention may be bound on glass, silica, semiconductor, magnetic particles, plastic, gold or silver tube, thin film, porous filter or bead to be used as a chip. And, the PNA conjugated with an amino acid spacer according to the present invention may be immobilized on a functionalized solid substance to manufacture an apparatus for detecting or analyzing sequence of nucleobases.

What is claimed is:

1. A peptide nucleic acid (PNA) conjugated with an amino acid spacer, which is represented by Chemical Formula 1:

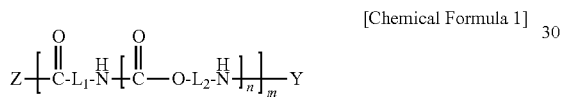

[Chemical Formula 1]

wherein

Z is a PNA oligomer with 8 to 40 nucleobases, and the amine (N)-terminus of the PNA oligomer is bonded to a carbonyl group;

$L_1$ and $L_2$ are independently a chemical bond or linear or branched $C_1$-$C_{15}$ alkylene, and the carbon atom of the alkylene may be further substituted with 1 to 8 oxygen (O) atom(s);

Y is hydrogen or a linker for immobilization onto a support; and m and n are independently an integer from 1 to 10.

2. The PNA conjugated with an amino acid spacer according to claim 1, wherein $L_1$ is —$CH_2$—, $L_2$ is —$CH_2CH_2OCH_2CH_2$—, m is an integer from 1 to 3, and n is 2, 4 or 6.

3. The PNA conjugated with an amino acid spacer according to claim 1, wherein Y is a linker of the following structure:

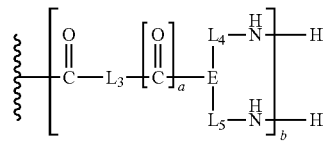

wherein $L_3$, $L_4$ and $L_5$ are independently a chemical bond or $C_1$-$C_{10}$ alkylene, and the carbon atom of the alkylene may be further substituted with 1 to 3 oxygen atom(s);

E is CH or N;

a is 0 or 1; and b is an integer from 2 to 10.

4. The PNA conjugated with an amino acid spacer according to claim 3, wherein Y is selected from the following structures:

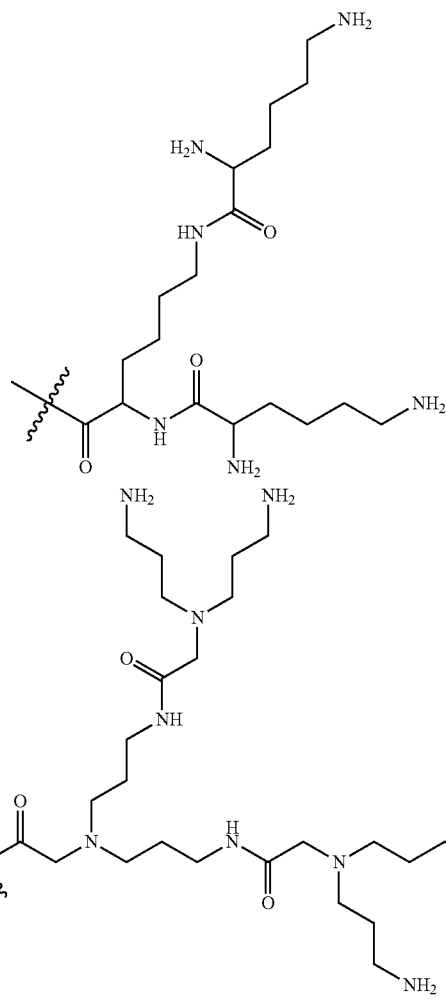

-continued

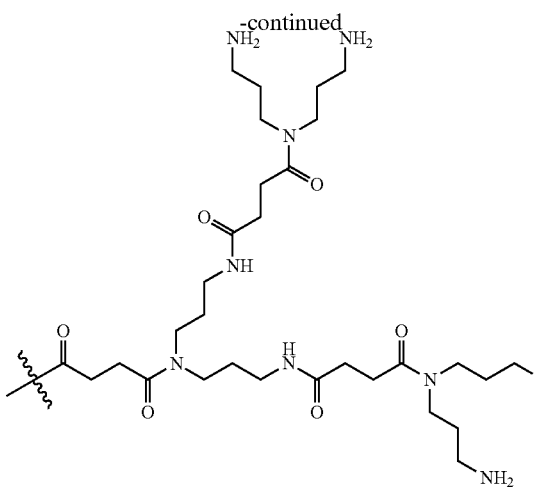

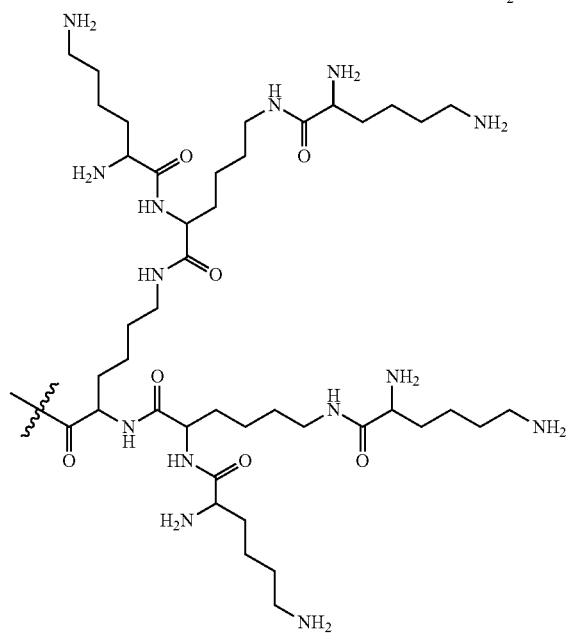

5. An amino acid spacer monomer represented by Chemical Formula 2:

[Chemical Formula 2]

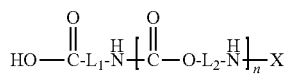

wherein
$L_1$ and $L_2$ are independently a chemical bond or linear or branched $C_1$-$C_{15}$ alkylene, and the carbon atom of the alkylene may be further substituted with 1 to 8 oxygen atom(s);
X is hydrogen or an amine protecting group; and
n is an integer from 1 to 10.

6. The amino acid spacer monomer according to claim 5, wherein the amine protecting group X is t-butoxycarbonyl (Boc), 9H-fluoren-9-ylmethoxycarbonyl (Fmoc), trityl, benzyl, chloroacetyl, benzyloxycarbonyl, p-methoxybenzyloxycarbonyl, formyl, trifluoroacetyl, p-toluenesulfonyl, benzenesulfonyl, methanesulfonyl, p-nitrobenzyloxycarbonyl or 2,2,2- trichloroethoxycarbonyl.

7. A method for preparing a PNA conjugated with an amino acid spacer, comprising sequentially reacting a PNA oligomer having 8 to 40 nucleobases with an amino acid spacer monomer represented by Chemical Formula 2 to prepare a PNA conjugated with an amino acid spacer, which is represented by Chemical Formula 3:

[Chemical Formula 2]

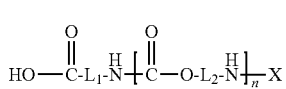

[Chemical Formula 3]

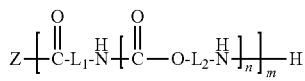

wherein
Z, $L_1$, $L_2$, m and n are the same as defined in claim 1; and
X is an amine protecting group.

8. The method for preparing a PNA conjugated with an amino acid spacer according to claim 7, wherein a PNA conjugated with an amino acid spacer, which is represented by Chemical Formula 3, is sequentially reacted with an immobilization linker represented by Chemical Formula 4 to prepare a PNA conjugated with an amino acid spacer with the immobilization linker attached, which is represented by Chemical Formula 5:

[Chemical Formula 3]

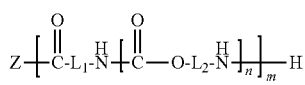

[Chemical Formula 4]

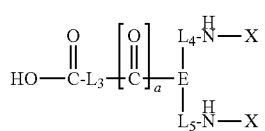

[Chemical Formula 5]

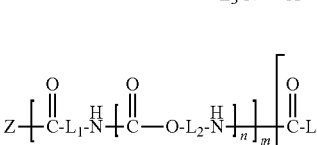

wherein
Z, $L_1$, $L_2$, m and n are the same as defined in claim 1;
$L_3$, $L_4$ and $L_5$ are independently a chemical bond or $C_1$-$C_{10}$ alkylene, and the carbon atom of the alkylene may be further substituted with 1 to 3 oxygen atom(s);
E is CH or N;
X is an amine protecting group;
a is 0 or 1; and
b is an integer from 2 to 10.

9. A method for immobilizing the PNA conjugated with an amino acid spacer according to claim 1 on the solid surface of a glass substrate, silica, semiconductor, magnetic particles, nylon, poly(dimethylsiloxane) (PDMS), thin film (membrane), cellulose or nitrocellulose on which an aldehyde group, a carboxyl group, an epoxy group, an isothiocyanate group, an N-hydroxysuccinimidyl (NHS) group or an activated ester group is exposed.

10. A kit for analysis, detection or regulation of nucleic acids, comprising the PNA conjugated with an amino acid spacer according to claim 1.

11. The kit for analysis, detection or control of nucleic acids according to claim 10, wherein the PNA is bound to glass, silica, magnetic particles, semiconductor, plastic, gold or silver tube, thin film, porous filter or bead.

12. An apparatus for analysis or detection of nucleic acids, comprising the PNA conjugated with an amino acid spacer according to claim 1.

13. The apparatus for analysis or detection of nucleic acids according to claim 12, wherein the PNA is bound to glass, silica, magnetic particles, semiconductor, plastic, gold or silver tube, thin film, porous filter or bead.

14. A method for analyzing, detecting, or controlling nucleic acids comprising:
   contacting a PNA conjugated with an amino acid spacer with a nucleic acid sample, wherein the PNA conjugated with the amino acid spacer is represented by Chemical Formula 1,

[Chemical Formula 1]

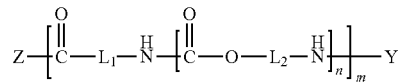

and wherein

Z is a PNA oligomer with 8 to 40 nucleobases, and the amine (N)-terminus of the PNA oligomer is bonded to a carbonyl group $L_1$ and $L_2$ are independently a chemical bond or linear or branched $C_1$-$C_{15}$ alkylene, and the carbon atom of the alkylene may be further substituted with 1 to 8 oxygen (O) atoms;

Y is hydrogen or a linker for immobilization onto a support; and m and n are independently an integer from 1 to 10.

* * * * *

UNITED STATES PATENT AND TRADEMARK OFFICE
CERTIFICATE OF CORRECTION

PATENT NO. : 8,450,469 B2  
APPLICATION NO. : 12/810453  
DATED : May 28, 2013  
INVENTOR(S) : Hyunil Lee et al.

Page 1 of 1

It is certified that error appears in the above-identified patent and that said Letters Patent is hereby corrected as shown below:

Title Page, Column 2, OTHER PUBLICATIONS, Line 1, delete "eta l." and insert -- et al. --

Title Page 2, Column 1, OTHER PUBLICATIONS, Line 16, delete "Labeifree" and insert -- Labelfree --

In the Claims

Column 35, Line 43, Claim 4, after " 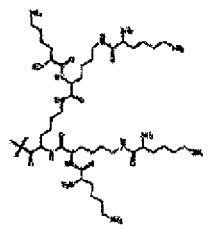 " insert -- . --

Column 35, Line 64, Claim 6, delete "chioroacetyl" and insert -- chloroacetyl --

Column 38, Line 11, Claim 14, delete "group" and insert -- group; --

Column 38, Line 11, Claim 14, delete "L2are" and insert -- L2 are --

Signed and Sealed this  
Fifth Day of November, 2013

Teresa Stanek Rea  
*Deputy Director of the United States Patent and Trademark Office*

SEQUENCE LISTING

<160> NUMBER OF SEQ ID NOS: 32

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ccatcatctt gggctttcgc                                        20

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
caaaagaaaa ttaggtaaca gcggta                                 26

<210> SEQ ID NO 3
<211> LENGTH: 20
<212> TYPE: DNA
<213> ORGANISM: Artificial Sequence
<220> FEATURE:
<223> OTHER INFORMATION: Primer

```
<400> SEQUENCE: 3
gtgctgcaag gcgattaagt                                          20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
attaggcacc ccaggcttta                                          20

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
gtccattcgc cattcagg                                            18

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
gagtcagtga gcgaggaagc                                          20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
agggaagaaa gcgaaaggag                                          20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
tttacggttc ctggcctttt                                          20

<210> SEQ ID NO 9
<211> LENGTH: 15
<212> TYPE: DNA
<213> ORGANISM: Artificial Sequence
<220> FEATURE:
<223> OTHER INFORMATION: Primer

<400> SEQUENCE: 9
tcatccatat aactg                                               15

<210> SEQ ID NO 10
<211> LENGTH: 15
```

```
<212> TYPE: DNA
<213> ORGANISM: Artificial Sequence
<220> FEATURE:
<223> OTHER INFORMATION: Primer

<400> SEQUENCE: 10
tcatccacat aactg                                                    15

<210> SEQ ID NO 11
<211> LENGTH: 15
<212> TYPE: DNA
<213> ORGANISM: Artificial Sequence
<220> FEATURE:
<223> OTHER INFORMATION: Primer

<400> SEQUENCE: 11
tcatccagat aactg                                                    15

<210> SEQ ID NO 12
<211> LENGTH: 15
<212> TYPE: DNA
<213> ORGANISM: Artificial Sequence
<220> FEATURE:
<223> OTHER INFORMATION: Primer

<400> SEQUENCE: 12
tcatccaaat aactg                                                    15

<210> SEQ ID NO 13
<211> LENGTH: 15
<212> TYPE: DNA
<213> ORGANISM: Artificial Sequence
<220> FEATURE:
<223> OTHER INFORMATION: Primer

<400> SEQUENCE: 13
tcatccatat aactg                                                    15

<210> SEQ ID NO 14
<211> LENGTH: 15
<212> TYPE: DNA
<213> ORGANISM: Artificial Sequence
<220> FEATURE:
<223> OTHER INFORMATION: Primer

<400> SEQUENCE: 14
tcatccacat aactg                                                    15

<210> SEQ ID NO 15
<211> LENGTH: 15
<212> TYPE: DNA
<213> ORGANISM: Artificial Sequence
<220> FEATURE:
<223> OTHER INFORMATION: Primer

<400> SEQUENCE: 15
tcatccagat aactg                                                    15

<210> SEQ ID NO 16
<211> LENGTH: 15
<212> TYPE: DNA
<213> ORGANISM: Artificial Sequence
<220> FEATURE:
<223> OTHER INFORMATION: Primer

<400> SEQUENCE: 16
tcatccaaat aactg                                                    15
```

<210> SEQ ID NO 17
<211> LENGTH: 15
<212> TYPE: DNA
<213> ORGANISM: Artificial Sequence
<220> FEATURE:
<223> OTHER INFORMATION: Primer

<400> SEQUENCE: 17
tcatccatat aactg                                                      15

<210> SEQ ID NO 18
<211> LENGTH: 15
<212> TYPE: DNA
<213> ORGANISM: Artificial Sequence
<220> FEATURE:
<223> OTHER INFORMATION: Primer

<400> SEQUENCE: 18
tcatccacat aactg                                                      15

<210> SEQ ID NO 19
<211> LENGTH: 15
<212> TYPE: DNA
<213> ORGANISM: Artificial Sequence
<220> FEATURE:
<223> OTHER INFORMATION: Primer

<400> SEQUENCE: 19
tcatccagat aactg                                                      15

<210> SEQ ID NO 20
<211> LENGTH: 15
<212> TYPE: DNA
<213> ORGANISM: Artificial Sequence
<220> FEATURE:
<223> OTHER INFORMATION: Primer

<400> SEQUENCE: 20
tcatccaaat aactg                                                      15

<210> SEQ ID NO 21
<211> LENGTH: 15
<212> TYPE: DNA
<213> ORGANISM: Artificial Sequence
<220> FEATURE:
<223> OTHER INFORMATION: Primer

<400> SEQUENCE: 21
tcatccatat aactg                                                      15

<210> SEQ ID NO 22
<211> LENGTH: 15
<212> TYPE: DNA
<213> ORGANISM: Artificial Sequence
<220> FEATURE:
<223> OTHER INFORMATION: Primer

<400> SEQUENCE: 22
tcatccacat aactg                                                      15

<210> SEQ ID NO 23
<211> LENGTH: 15
<212> TYPE: DNA
<213> ORGANISM: Artificial Sequence
<220> FEATURE:
<223> OTHER INFORMATION: Primer

```
<400> SEQUENCE: 23
tcatccagat aactg                                                         15

<210> SEQ ID NO 24
<211> LENGTH: 15
<212> TYPE: DNA
<213> ORGANISM: Artificial Sequence
<220> FEATURE:
<223> OTHER INFORMATION: Primer

<400> SEQUENCE: 24
tcatccaaat aactg                                                         15

<210> SEQ ID NO 25
<211> LENGTH: 15
<212> TYPE: DNA
<213> ORGANISM: Artificial Sequence
<220> FEATURE:
<223> OTHER INFORMATION: Primer

<400> SEQUENCE: 25
tcatccatat aactg                                                         15

<210> SEQ ID NO 26
<211> LENGTH: 15
<212> TYPE: DNA
<213> ORGANISM: Artificial Sequence
<220> FEATURE:
<223> OTHER INFORMATION: Primer

<400> SEQUENCE: 26
tcatccacat aactg                                                         15

<210> SEQ ID NO 27
<211> LENGTH: 15
<212> TYPE: DNA
<213> ORGANISM: Artificial Sequence
<220> FEATURE:
<223> OTHER INFORMATION: Primer

<400> SEQUENCE: 27
tcatccagat aactg                                                         15

<210> SEQ ID NO 28
<211> LENGTH: 15
<212> TYPE: DNA
<213> ORGANISM: Artificial Sequence
<220> FEATURE:
<223> OTHER INFORMATION: Primer

<400> SEQUENCE: 28
tcatccaaat aactg                                                         15

<210> SEQ ID NO 29
<211> LENGTH: 205
<212> TYPE: DNA
<213> ORGANISM: Human Hepatitis B Virus

<400> SEQUENCE: 29
ccatcatctt gggctttcgc aagattccta tgggagtggg cctcagtccg tttctctggc        60
tcagtttact agtgccattt gttcagtggt tcgtagggct ttcccccact gtttggcttt       120
cagttatatg gatgatgtgg tattgagggc caagtctgta caacatcttg aatccctttt       180
taccactgtt accaattttc ttttg                                             205
```

<210> SEQ ID NO 30
<211> LENGTH: 545
<212> TYPE: DNA
<213> ORGANISM: Human Hepatitis B Virus

<400> SEQUENCE: 30

```
gtgctgcaag gcgattaagt tgggtaacgc cagggttttc ccagtcacga cgttgtaaaa        60
cgacggccag tgaattgtaa tacgactcac tatagggcga attgggcccg acgtcgcatg       120
ctcccggccg ccatggccgc ggggggggatc catcatcttg gctttcgca agattcctat       180
gggagtgggc ctcagtccgt ttctcctggc tcagtttact agtgccattt gttcagtggt       240
tcgtagggct ttcccccact gtttggcttc agttatatgg atgatgtggt attgagggcc       300
aagtctgtac aacatcttga atcccttttt accactgtta ccaattttct tttgatcact       360
agtgcggccg cctgcaggtc gaccatatgg gagagctccc aacgcgttgg atgcatagct       420
tgagtattct atagtgtcac taaatagct tggcgtaatc atggtcatag ctgtttcctg        480
tgtgaaattg ttatccgctc acaattccac acaaagcata agtgtaaag cctggggtgc        540
ctaat                                                                    545
```

<210> SEQ ID NO 31
<211> LENGTH: 779
<212> TYPE: DNA
<213> ORGANISM: Human Hepatitis B Virus

<400> SEQUENCE: 31

```
gtccattcgc cattcaggct gcgtcaactg ttgggaaggg cgatcggtgc gggcctcttc        60
gctattacgc cagctggcga aagggatgtg ctgcaaggcg attaagttgg gtaacgccag       120
ggttttccca gtcacgacgt tgtaaaacga cggccagtga attgtaatac gactcactat       180
agggcgaatt gggcccgacg tcgcatgctc ccggccgcca tggccgcggg atccatcatc       240
ttgggctttc gcaagattcc tatgggagtg gcctcagtc cgtttctcct ggctcagttt       300
actagtgcca tttgttcagt ggttcgtagg gctttccccc actgtttggc tttcagttat       360
atggatgatg tggtattgag ggccaagtct gtacaacatc tgaatcccctt tttaccactg       420
ttaccaattt tcttttgatc actagtgcgg ccgcctgcag gtcgaccata tgggagagct       480
cccaacgcgt tggatgcata gcttgagtat tctatagtgt cacctaaata gcttggcgta       540
atcatggtca tagctgtttc ctgtgtgaaa ttgttatccg ctcacaattc cacacaaagc       600
ataaagtgta aagcctgggg tgcctaatga gtgagctaac tcacattaat tgcgttgcgc       660
tcactgcccg ctttccagtc gggaaacctg tcgtgccagc tgcattaatg aatcggccaa       720
cgcgcgggga gaggcggttt gcgtattggg cgctcttccg cttcctcgct cactgactc       779
```

<210> SEQ ID NO 32
<211> LENGTH: 998
<212> TYPE: DNA
<213> ORGANISM: Human Hepatitis B Virus

<400> SEQUENCE: 32

```
agggaagaaa gcgaaaggag cgggcgctag ggcgctggca agtgtagcgg tcacgctgcg        60
cgtaaccacc acacccgccg cgcttaatgc gccgctacag gcgcgtcca ttcgccattc       120
aggctgcgca actgttggga agggcgatcg gtgcgggcct cttcgctatt acgccagctg       180
gcgaaaggga tgtgctgcaa ggcgattaag ttgggtaacg ccaggttttt cccagtcacg       240
acgttgtaaa acgacggcca gtgaattgta atacgactca ctatagggcg aattgggccc       300
```

```
gacgtcgcat gctcccggcc gccatggccg cgggatccat catcttgggc tttcgcaaga    360
ttcctatggg agtgggcctc cagtccgttt ctcctggctc agtttactag tgccatttgt    420
tcagtggttc gtagggcttt cccccactgt ttggctttca gttatatgga tgatgtggta    480
ttgagggcca agtctgtaca acatcttgaa tccctttta ccactgttac caattttctt     540
ttgatcacta gtgcggccgc ctgcaggtcg accatatggg agagctccca acgcgttgga    600
tgcatagctt gagtattcta tagtgtcacc taaatagctt ggcgtaatca tggtcatagc    660
tgtttcctgt gtgaaattgt tatccgctca caattccaca caaagcataa agtgtaaagc    720
ctggggtgcc taatgagtga gctaactcac attaattgcg ttgcgctcac tgcccgcttt    780
ccagtcggga aacctgtcgt gccagctgca ttaatgaatc ggccaacgcg cggggagagg    840
cggtttgcgt attgggcgct cttccgcttc ctcgctcact gactcgctgc gctcggtcgt    900
tcggctgcgg cgagcggtat cagctcactc aaaggcggta atacggttat ccacagaatc    960 agggataac gcaggaaaga acatgtgagc aaaaggcc                             998
```